(12) United States Patent
Yamamoto et al.

(10) Patent No.: US 9,233,814 B2
(45) Date of Patent: Jan. 12, 2016

(54) MANUFACTURING DEVICE FOR COMPOSITE BODIES OF CONTINUOUS SHEET-LIKE MEMBERS

(75) Inventors: Hiroki Yamamoto, Kagawa (JP); Hidefumi Goda, Kagawa (JP)

(73) Assignee: Unicharm Corporation, Ehime (JP)

( * ) Notice: Subject to any disclaimer, the term of this patent is extended or adjusted under 35 U.S.C. 154(b) by 720 days.

(21) Appl. No.: 13/634,908

(22) PCT Filed: Mar. 11, 2011

(86) PCT No.: PCT/JP2011/055729
§ 371 (c)(1),
(2), (4) Date: Nov. 20, 2012

(87) PCT Pub. No.: WO2011/115001
PCT Pub. Date: Sep. 22, 2011

(65) Prior Publication Data
US 2013/0079207 A1     Mar. 28, 2013

(30) Foreign Application Priority Data
Mar. 16, 2010    (JP) .................................. 2010-059556

(51) Int. Cl.
*B65H 37/04*    (2006.01)
*A61F 13/15*    (2006.01)
(Continued)

(52) U.S. Cl.
CPC .......... *B65H 37/04* (2013.01); *A61F 13/15764* (2013.01); *B65H 35/08* (2013.01);
(Continued)

(58) Field of Classification Search
CPC ........ B65H 37/00; B65H 37/04; B65H 35/08; B65H 39/14; B65H 39/16; B65H 2801/57; B65H 2301/33216; B65H 2301/33222; B65H 2406/345; B65H 37/002; B65H 37/02; B65H 39/065; A61F 13/15764; A61F 13/15747; B31B 41/00; B31B 21/00; B31B 2221/10; B31B 2221/20; B31B 2221/402; B31B 2241/007; B31B 29/00
See application file for complete search history.

(56) References Cited

U.S. PATENT DOCUMENTS

| 4,265,410 A * | 5/1981 | Fanning | ................. | H01G 13/02 |
|  |  |  |  | 242/524.1 |
| 4,532,750 A * | 8/1985 | Meier | .................. | B65H 29/006 |
|  |  |  |  | 242/528 |

(Continued)

FOREIGN PATENT DOCUMENTS

| CN | 1085494 A | 4/1994 |
| CN | 1308923 A | 8/2001 |

(Continued)

OTHER PUBLICATIONS

International Search Report based on corresponding PCT application No. PCT/JP2011/055729 dated Jun. 14, 2011 (4 pgs).

(Continued)

*Primary Examiner* — Thanh Truong
*Assistant Examiner* — Thomas M Wittenschlaeger
(74) *Attorney, Agent, or Firm* — Brinks Gilson & Lione

(57) ABSTRACT

A device for manufacturing a composite body of a continuous sheet-like member by attaching and handing over a retained workpiece to a continuous sheet-like member, at a workpiece hand over position including a rotating body that rotates about a rotating shaft, a workpiece retaining portion supported by the rotating body in a state where a retaining surface that retains the workpiece faces outward in a direction of radius of gyration of the rotating body, a workpiece hand over mechanism that is positioned to accord with the workpiece hand over position along a direction of rotation of the rotating body, and that hands over the workpiece from the retaining surface to the continuous sheet-like member when the retaining surface passes the workpiece hand over position, wherein the workpiece hand over mechanism has a roller that comes into contact with the continuous sheet-like member to transport the continuous sheet-like member, and a pushing mechanism that is capable of pushing out an outer circumferential face of the roller inward along the direction of radius of gyration to push the continuous sheet-like member against the workpiece, and the pushing mechanism changes an amount by which the outer circumferential face is pushed out in conjunction with a location, of the retaining surface along the direction of radius of gyration, at the workpiece hand over position.

8 Claims, 13 Drawing Sheets

(51) Int. Cl.
    *B65H 35/08*   (2006.01)
    *B65H 39/14*   (2006.01)
(52) U.S. Cl.
    CPC ..... *B65H 39/14* (2013.01); *B65H 2301/33216* (2013.01); *B65H 2301/33222* (2013.01); *B65H 2406/345* (2013.01); *B65H 2801/57* (2013.01)

(56) References Cited

U.S. PATENT DOCUMENTS

| | | | |
|---|---|---|---|
| 4,726,876 A * | 2/1988 | Tomsovic, Jr. | A61F 13/15601 156/552 |
| 4,767,487 A * | 8/1988 | Tomsovic, Jr. | A61F 13/15601 156/256 |
| 4,880,102 A * | 11/1989 | Indrebo | A61F 13/15764 198/418.3 |
| 5,025,910 A * | 6/1991 | Lasure | A61F 13/15764 198/377.04 |
| 6,022,443 A * | 2/2000 | Rajala | A61F 13/15764 156/302 |
| 6,139,004 A * | 10/2000 | Couillard | B65H 29/242 271/188 |
| 6,352,607 B1 * | 3/2002 | Kuen | A61F 13/15764 156/204 |
| 6,475,325 B1 | 11/2002 | Parrish et al. | |
| 2002/0023723 A1 * | 2/2002 | Blumenthal | A61F 13/15764 156/530 |
| 2003/0066609 A1 | 4/2003 | Calvert | |
| 2004/0087425 A1 * | 5/2004 | Ng | A61F 13/15756 493/222 |
| 2004/0089516 A1 | 5/2004 | Christian et al. | |
| 2006/0047258 A1 * | 3/2006 | Schneider | A61F 13/15756 604/385.27 |
| 2008/0066853 A1 | 3/2008 | Schiebout | |
| 2008/0196564 A1 * | 8/2008 | McCabe | A61F 13/15723 83/23 |

FOREIGN PATENT DOCUMENTS

| | | |
|---|---|---|
| CN | 1880059 A | 12/2006 |
| CN | 101528167 A | 9/2009 |
| EP | 0 355 292 A2 | 4/1985 |
| EP | 2 135 591 A1 | 12/2009 |
| GB | 2 208 878 A | 8/1988 |
| JP | 1-141712 | 9/1989 |
| JP | 2004/148040 A | 5/2004 |
| JP | 2007-508220 A | 4/2007 |
| JP | 2008-253633 | 10/2008 |
| JP | 2009-282887 | 12/2009 |
| WO | WO 97/06299 | 2/1997 |
| WO | WO 2005/065617 A1 | 7/2005 |

OTHER PUBLICATIONS

Chinese Official Action from corresponding Chinese application No. 201180014371.X dated Jul. 29, 2014 (8 pgs).
European Office Communication from corresponding European application No. 11756187.8 dated 104/9/2014 (4 pgs).
Mexican Office Communication and English translation from corresponding Mexican application No. 27108 date Mar. 27, 2014 (6 pgs).
European extended Search Report from corresponding European application No. 11756187.8 dated Dec. 20, 2013 (6 pgs).
Eurasian Office Communication and translation from corresponding Eurasian application No. 201201297/31 dated Apr. 29, 2014 (4 pgs).

* cited by examiner

SECTION B-B

B-B SIDE VIEW

C-C SIDE VIEW

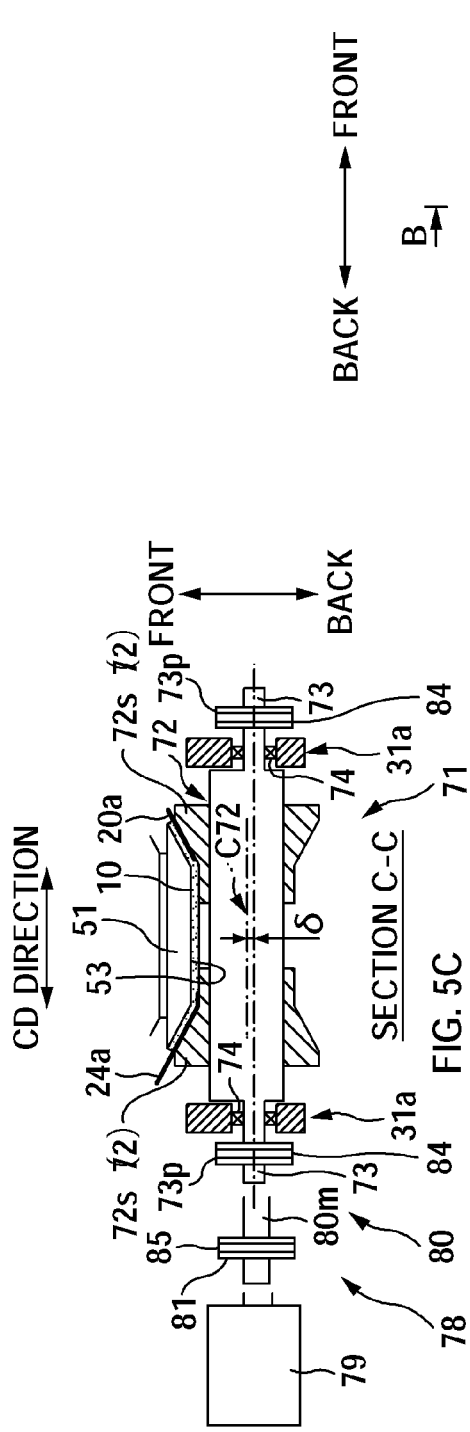
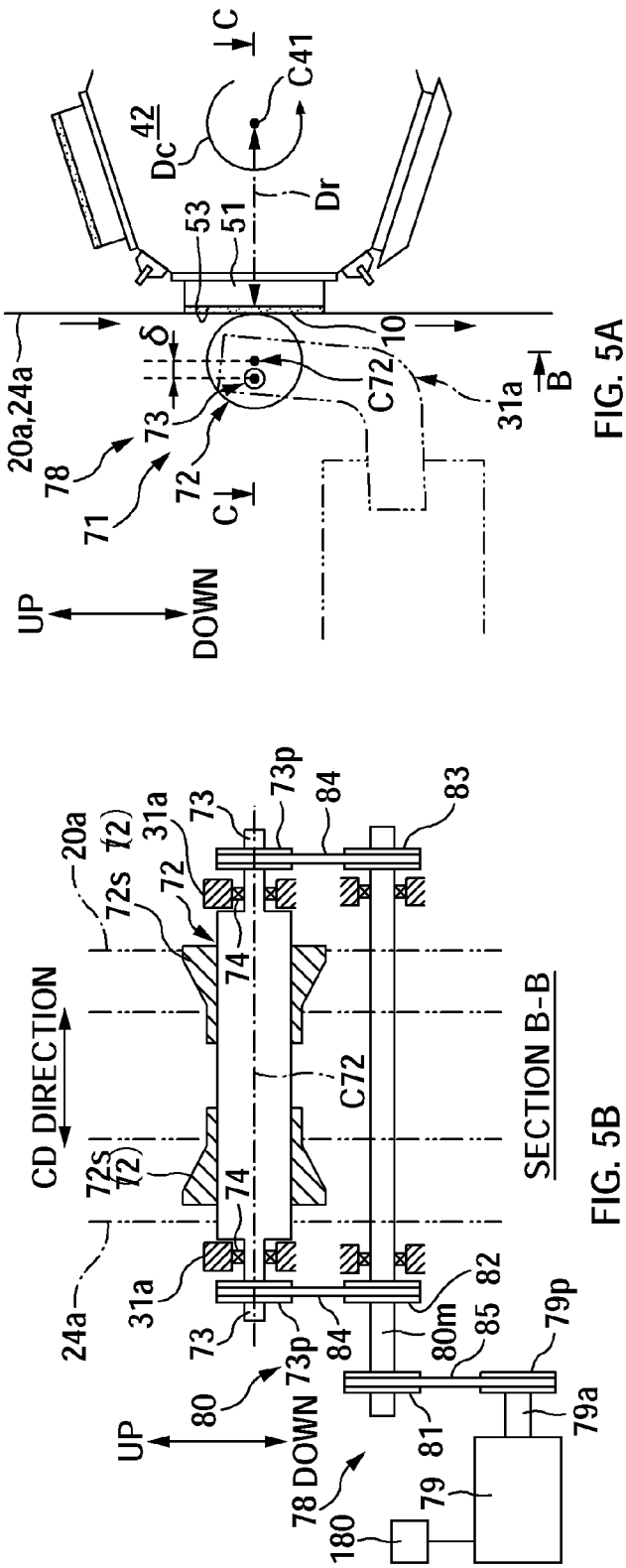
FIG. 5A
FIG. 5B
FIG. 5C

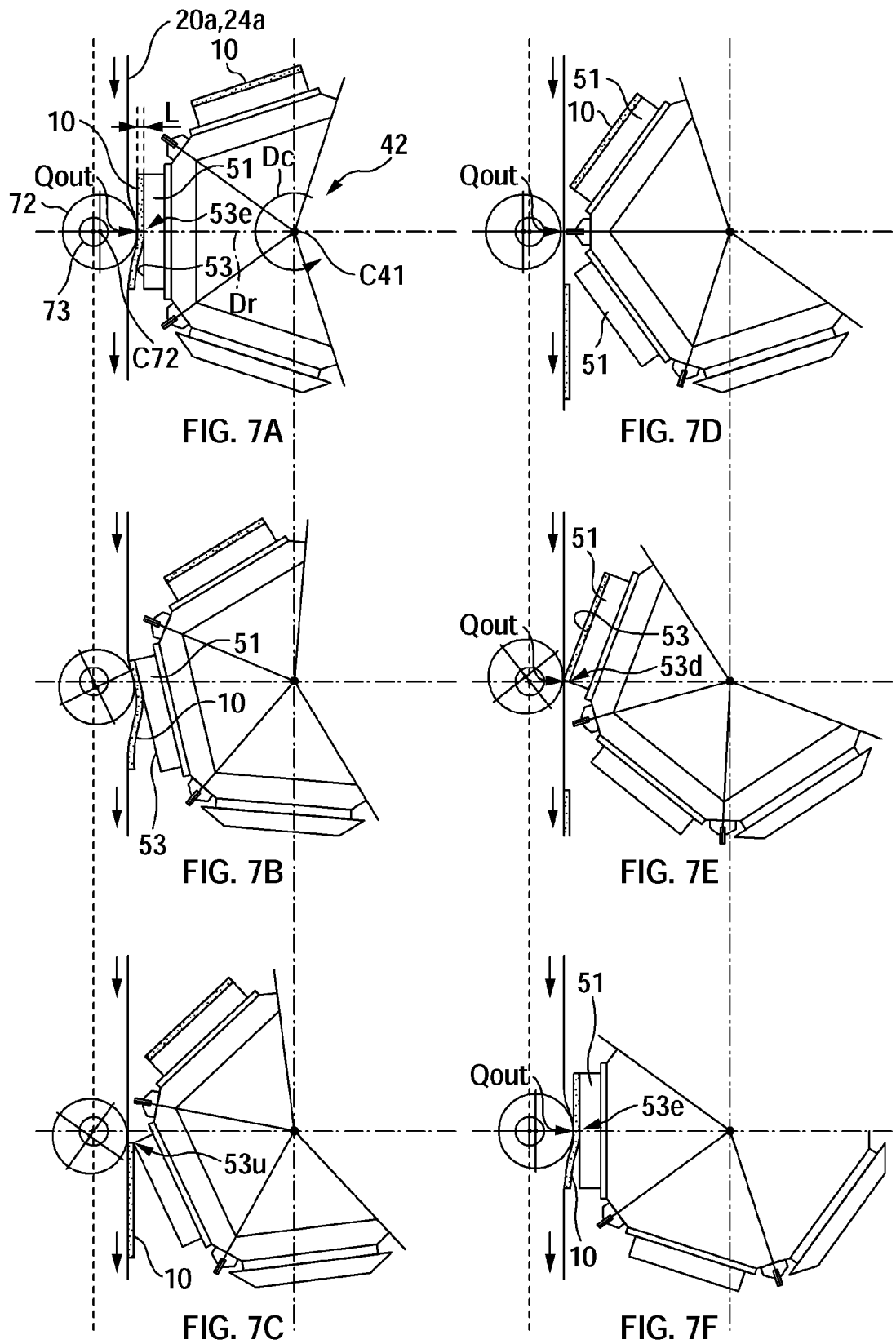

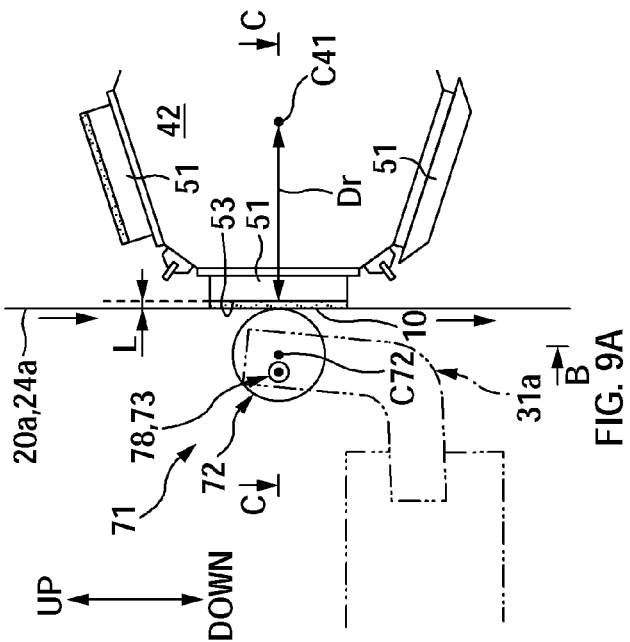
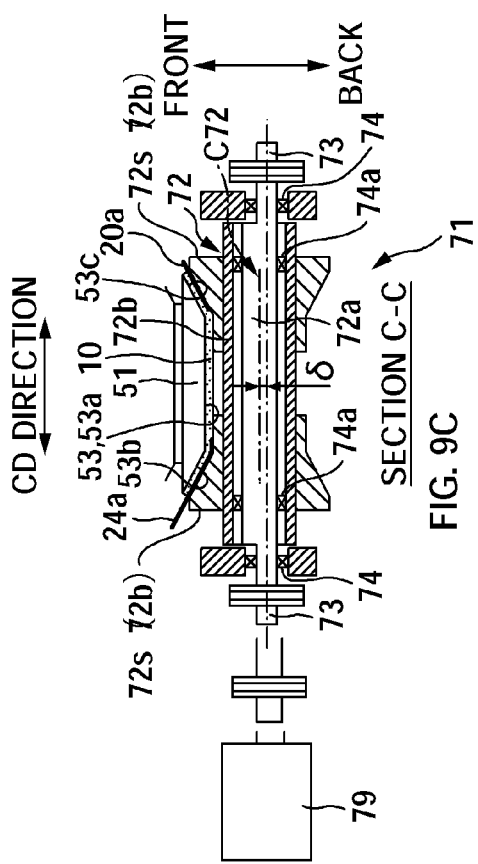
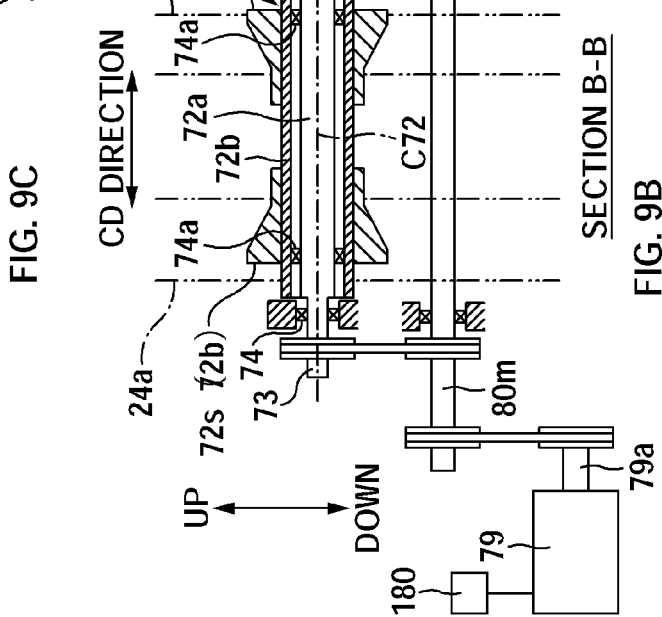

MANUFACTURING DEVICE FOR COMPOSITE BODIES OF CONTINUOUS SHEET-LIKE MEMBERS

RELATED APPLICATION

The present application is a 35 U.S.C. §371 national stage filing of International Patent Application No. PCT/JP2011/055729, filed Mar. 11, 2011, to which priority is claimed under 35 U.S.C. §120 and through which priority is claimed under 35 U.S.C. §119 to Japanese Priority Patent Application No. 2010-059556, filed Mar. 16, 2010.

TECHNICAL FIELD

The present invention relates to a manufacturing device for composite bodies of continuous sheet-like members used for manufacturing absorbent articles such as disposable diapers and the like.

BACKGROUND ART

Conventionally, workpieces are bonded to continuous sheet-like members along manufacturing lines for absorbent articles such as disposable diapers. And a rotating drum apparatus is used for the bonding process (PTL 1).

CITATION LIST

Patent Literature

[PTL 1]
Japanese Patent Application Laid-open Publication No. 2004-148040

SUMMARY OF INVENTION

Technical Problem

As in the side view shown in FIG. 6A, the rotating drum apparatus has a rotating body 42 that rotates about the rotation axis C41. The rotating body 42 has a retaining surface 53 that retains the workpiece 10. The retaining surface 53 is provided to the rotating body 42 in a state facing the outside along the direction of the radius of gyration Dr of the rotating body 42. And in direction Dc in which the rotating body 42 rotates there are set a workpiece receiving position Qin (not shown in FIGS. 6A and 6B) where the workpiece 10 is received, and a workpiece hand over position Qout where the workpiece 10 is handed over to the continuous sheet-like members 20a, 24a. Further, a roller 172 is positioned at the workpiece hand over position Qout where the continuous sheet-like members 20a, 24a are made to come into contact with the roller 172 to be transported. Therefore, when the retaining surface 53 passes the workpiece hand over position Qout, the workpiece 10 retained by the retaining surface 53 is bonded to the continuous sheet-like member 20a, 24a to be handed over from the retaining surface 53 to the continuous sheet-like member 20a, 24a.

By the way, taking into consideration the stability and the like when receiving the workpiece 10, this retaining surface 53 is configured with, for example, a flat surface as the main surface.

However, when handing over the workpiece 10, the distance L between the roller 172 is partially varied during hand over due to this planar surface and thus there is fear that the state of bonding may be disturbed. Specifically, as shown in FIGS. 6A and 6B, the radiuses of gyration Rd, Re around the rotation axis C41 at the downstream end portion 53d (or upstream end portion 53u) along the aforementioned rotation direction Dc of the retaining surface 53 and the center portion 53e differ from each other. With this being the situation, when the downstream end portion 53d (or upstream end portion 53u) passes the hand over position Qout as shown in FIG. 6A, the distance Ld between this end portion 53d and the outer circumferential face of the roller 172 would greatly differ from the distance Le between the center portion 53e and the outer circumferential face of the roller 172 when this center portion 53e passes the hand over position Qout, as shown in FIG. 6B.

As a result, when the roller 172 is set to be appropriately pushed against the downstream end portion 53d (or upstream end portion 53u), a large gap is formed at the center portion 53e avoiding effective pushing as shown in FIG. 6B. And on the other hand, there is fear that the downstream end portion 53d is excessively pushed when the center portion 53e is appropriately pushed. Hence, poor bonding is likely to occur.

Note that, such problem is not limited to the case when the geometry of the surface is planar. In other words, such problem would occur on one level or the other when the geometry of the surface of the retaining surface 53 does not have an arc-shape with a radius of curvature with the above-mentioned radius of gyration Rd or Re.

The present invention has been made in view of the conventional problems such as those mentioned above, and an object thereof is to improve the stability when bonding and handing over workpieces retained by the retaining surface to the continuous sheet-like member.

Solution to Problem

In order to solve the above-described problem, a principal aspect of the invention is, a device for manufacturing a composite body of a continuous sheet-like member by attaching and handing over a retained workpiece to a continuous sheet-like member, at a workpiece hand over position, including:

a rotating body that rotates about a rotating shaft;

a workpiece retaining portion supported by the rotating body in a state where a retaining surface that retains the workpiece faces outward in a direction of radius of gyration of the rotating body;

a workpiece hand over mechanism that is positioned to accord with the workpiece hand over position along a direction of rotation of the rotating body, and that hands over the workpiece from the retaining surface to the continuous sheet-like member when the retaining surface passes the workpiece hand over position, wherein the workpiece hand over mechanism has a roller that comes into contact with the continuous sheet-like member to transport the continuous sheet-like member, and a pushing mechanism that is capable of pushing out an outer circumferential face of the roller inward along the direction of radius of gyration to push the continuous sheet-like member against the workpiece, and the pushing mechanism changes an amount by which the outer circumferential face is pushed out in conjunction with a location, of the retaining surface along the direction of radius of gyration, at the workpiece hand over position.

Features of the invention other than the above will become clear from the description of the present specification and the drawings attached.

Advantageous Effects of Invention

According to the present invention, it is possible to improve the stability when bonding and handing over workpieces retained by the retaining surface to the continuous sheet-like member.

BRIEF DESCRIPTION OF DRAWINGS

FIG. 5A is a schematic side view of the hand over mechanism 71.

FIG. 5B is a sectional view taken along line B-B of FIG. 5A.

FIG. 5C is a sectional view taken along line C-C of FIG. 5A.

FIG. 7A is an explanatory diagram showing an operation of eccentric rotation.

FIG. 7B is an explanatory diagram showing an operation of eccentric rotation.

FIG. 7C is an explanatory diagram showing an operation of eccentric rotation.

FIG. 7D is an explanatory diagram showing an operation of eccentric rotation.

FIG. 7E is an explanatory diagram showing an operation of eccentric rotation.

FIG. 7F is an explanatory diagram showing an operation of eccentric rotation.

FIG. 9A is a schematic side view of a preferred aspect of the transport roller 72 associated with the hand over mechanism 71.

FIG. 9B is a sectional view taken along line B-B of FIG. 9A.

FIG. 9C is a sectional view taken along line C-C of FIG. 9A.

MODE FOR CARRYING OUT THE INVENTION

Figure 1A:
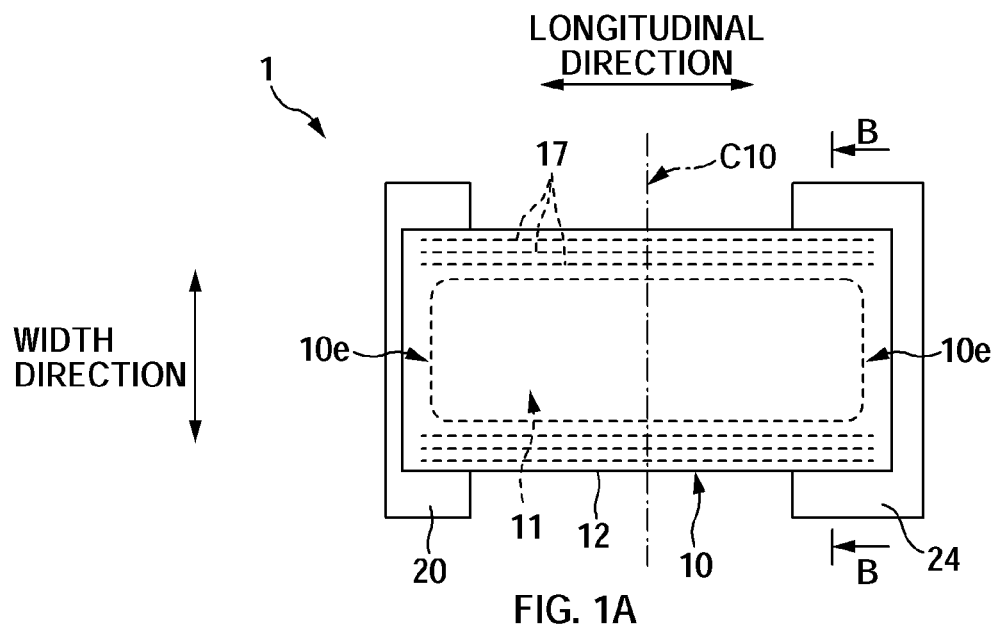
FIG. 1A is a planar view of a disposable diaper 1 in an unfolded state.

At least the following matters will be made clear from the description of the present specification with reference to the accompanying drawings.

A device for manufacturing a composite body of a continuous sheet-like member by attaching and handing over a retained workpiece to a continuous sheet-like member, at a workpiece hand over position according to the present invention includes a rotating body that rotates about a rotating shaft;

a workpiece retaining portion supported by the rotating body in a state where a retaining surface that retains the workpiece faces outward in a direction of radius of gyration of the rotating body;

a workpiece hand over mechanism that is positioned to accord with the workpiece hand over position along a direction of rotation of the rotating body, and that hands over the workpiece from the retaining surface to the continuous sheet-like member when the retaining surface passes the workpiece hand over position, wherein the workpiece hand over mechanism has a roller that comes into contact with the continuous sheet-like member to transport the continuous sheet-like member, and a pushing mechanism that is capable of pushing out an outer circumferential face of the roller inward along the direction of radius of gyration to push the continuous sheet-like member against the workpiece, and the pushing mechanism changes an amount by which the outer circumferential face is pushed out in conjunction with a location, of the retaining surface along the direction of radius of gyration, at the workpiece hand over position.

According to such a manufacturing device for composite bodies of continuous sheet-like members, the amount by which outer circumferential face of the roller is pushed out is changed in conjunction with the location of the retaining surface along the direction of the radius of gyration. Therefore, the variation in the distance between the outer circumferential face of the roller and the retaining surface can be restrained along approximately the entire length of the retaining surface in the direction of rotation. Thereby, the variation in the state in which the continuous sheet-like member is pushed against the workpiece when the retaining surface passes the hand over position can be effectively retrained. And as a result, the workpiece can be bonded and handed over to the continuous sheet-like member in a stable manner.

It is preferable that in the manufacturing device, the pushing mechanism increases an amount by which the outer circumferential face of the roller is pushed out at the workpiece hand over position when the location of the retaining surface moves inward along the direction of radius of gyration, and the pushing mechanism reduces an amount by which the outer circumferential face of the roller is pushed out when the location of the retaining surface moves outward along the direction of radius of gyration.

According to such a manufacturing device for composite bodies of continuous sheet-like members, the variation in the distance between the retaining surface and the outer circumferential face of the roller that may be caused due to the movement of the position of the retaining surface in and out along the direction of the radius of gyration momentarily, when the retaining surface passes the workpiece hand over position can be effectively restrained.

It is preferable that in the manufacturing device, the pushing mechanism has a driving source that moves a location of the outer circumferential face of the roller inward and outward along the direction of radius of gyration and a controller that controls the driving source.

According to such a manufacturing device for composite bodies of continuous sheet-like members, the location of the outer circumferential face of the roller along the direction of the radius of gyration is adjusted by a controller. In other words, the amount by which the outer circumferential face of the roller is pushed out is actively adjusted. Therefore, flexibility in adjustment of the location of the above outer circumference is excellent and the adjustment to the optimum location is easy. As a result, the variation in the distance between the retaining surface and the outer circumferential face of the roller that may be created when the retaining surface passes the workpiece hand over position can be surely restrained.

It is preferable that in the manufacturing device, a plurality of the workpiece retaining portions are provided at a predetermined angular interval along a direction of rotation of the rotating body, the rotating shaft of the roller is parallel to the rotating shaft of the rotating body, the roller has as a rotating shaft, an eccentric shaft decentered from an axis center of the roller, and the driving source of the pushing mechanism is a motor that drives the roller to rotate with the eccentric shaft as a center of rotation, and the motor allows the roller to make a single rotation for each workpiece retaining portion.

According to such a manufacturing device for composite bodies of continuous sheet-like members, the aforementioned problem can be solved with a simple configuration of an eccentric shaft provided to a roller and a motor driving the roller to rotate with this eccentric shaft as the rotation center. In other words, the variation in the distance between the retaining surface and the outer circumferential face of the roller that may be created when the retaining surface passes the workpiece hand over position can be surely restrained.

It is preferable that in the manufacturing device, the roller has a core portion and an outer circumferential portion arranged to cover an outer circumference of the core portion, the outer circumferential portion is rotatably supported by a bearing member interposed between the outer circumferential portion and the core portion with a center of the core portion as the center of rotation, and the eccentric shaft is provided at a location decentered from the center of the core portion, and the core portion is driven to rotate with the eccentric shaft as a center of rotation.

According to such a manufacturing device for composite bodies of continuous sheet-like members, the roller being driven to rotate about the eccentric shaft at the central portion of the roller varying the amount by which the outer circumferential face of the roller is pushed out enables to surely restrain the variation in the distance between the retaining surface and the roller that may be generated when the retaining surface passes the workpiece hand over position.

Further, the outer circumferential portion of the roller can be freely and relatively rotated with respect to the central portion thereof. Therefore, when the outer circumferential surface of the roller moves with regard to the retaining surface with difference in relative velocity, this difference in relative velocity is absorbed by the relative rotation of the outer circumferential portion of this roller with regard to the central portion. As a result, poor bonding such as wrinkles made to the workpieces and continuous sheet-like members due to the difference in relative velocity can be effectively restrained.

It is preferable that in the manufacturing device, the retaining surface of the workpiece retaining portion at the workpiece hand over position has a shape where a central part in a direction along the rotating shaft than two end portions therealong protrudes outward along the direction of radius of gyration, and a contour shape of the roller is in a drum shape, corresponding to the shape of the retaining surface, where a central part in a direction along the rotating shaft of the roller is concaved than two end portions therealong.

According to such a manufacturing device for composite bodies of continuous sheet-like members, the contour of the roller being formed in a shape corresponding to the shape of the retaining surface allows the continuous sheet-like members to be pushed tightly against the workpieces along approximately the entire length of the retaining surface in the direction along the rotational shaft.

It is preferable that in the manufacturing device, the outer circumferential portion is configured with a plurality of cylindrical members arranged in a direction along the rotational shaft of the roller, and the cylindrical members are each rotatably supported by the core portion via bearing members each provided for respective ones of the cylindrical members.

According to such a manufacturing device for composite bodies of continuous sheet-like members, even when the difference in relative velocity between the retaining surface and each location at the outer circumferential face of the roller changes along the direction of the rotational shaft, since the cylindrical members corresponding to each location relatively rotates independently with regard to the central portion, poor bonding due to the difference in relative velocity can be effectively restrained.

It is preferable that in the manufacturing device, an angular velocity of the roller driven to rotate is changed in conjunction with a location, of the retaining surface along the direction of radius of gyration, at the workpiece hand over position.

According to such a manufacturing device for composite bodies of continuous sheet-like members, the angular velocity of the roller driven to rotate is varied in conjunction with the location of the retaining surface along the rotating direction thus the difference in relative velocity between the outer circumferential face of the roller and the retaining surface can be reduced.

It is preferable that in the manufacturing device, a surface layer portion of the outer circumferential face of the roller is formed by an elastic member having flexibility to deform elastically.

According to such a manufacturing device for composite bodies of continuous sheet-like members, even when there is difference in relative velocity between the outer circumferential face of the roller and the retaining surface, this difference in relative velocity can be absorbed by elastic deformation of the surface layer portion of the roller. As a result, poor bonding such as wrinkles made to the workpieces and continuous sheet-like members due to the difference in relative velocity can be effectively restrained.

—First Embodiment—

The manufacturing device 31 for composite bodies 1a of continuous sheet-like members according to the first embodiment is, for example, used in a manufacturing line for disposable diapers 1.

Figure 1B:
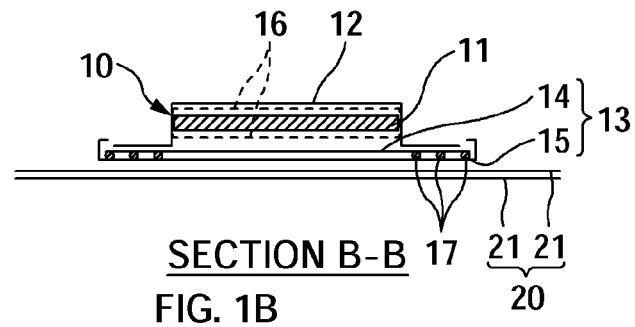
FIG. 1B is a sectional view taken along line B-B of FIG. 1A.
Figure 1C:
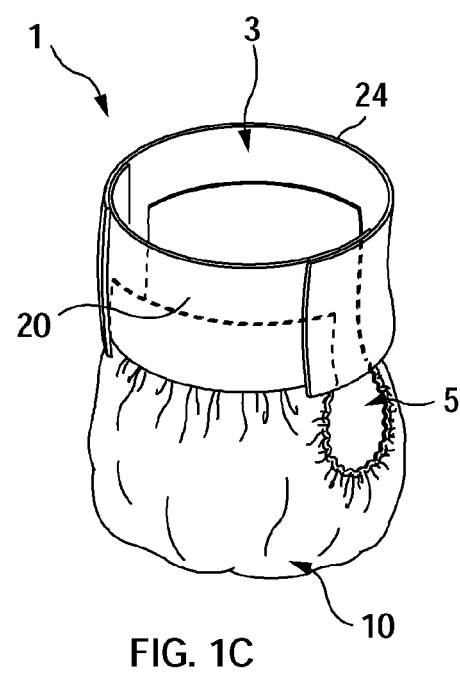
FIG. 1C is a perspective view of the diaper 1.

FIG. 1A through FIG. 1C are explanatory diagrams of disposable diapers. FIG. 1A is a planar view of a disposable diaper 1 in an unfolded state, FIG. 1B is a sectional view taken along line B-B of FIG. 1A, and FIG. 1C is a perspective view of the diaper 1.

This diaper 1 includes an abdominal side band member 20 that covers the abdominal side of the wearer, a back side band member 24 that covers the back side thereof, and a main absorbent body 10 that is set against the crotch when worn and that absorbs body fluid such as urine. In the unfolded state shown in FIG. 1A with the abdominal side band member 20 and the back side band member 24 spaced and aligned parallel with each other, the two end portions 10e, 10e in the longitudinal direction of the main absorbent body 10 are spanned therebetween and fixed thereto and its appearance configuration is in an approximately H shape seen in a planar view.

And from this state, when the main absorbent body 10 is folded into half at the center C10 in the longitudinal direction of the main absorbent body 10 and the band members 20, 24 opposing each other in the bi-fold state being fastened at portions to be in contact aside the wearer's abdomen, connects these band members 20, 24 in an annular form. In this way, a diaper 1 in a wearable state is formed with a body encircling opening 3 and a pair of leg encircling openings 5, 5 as shown in FIG. 1C.

Note that, a pants-type diaper is formed when a non-detachable connecting structure such as welding and the like is used for the above-described fastening structure whereas an openable diaper is formed when a detachable connecting structure such as a fastening tape member (not shown) and the like is used. Hereinafter, description of the components 10, 20, 24 of the diaper 1 will be given with reference to FIGS. 1A and 1B.

The main absorbent body 10 includes an absorbent body 11 made from liquid absorbent fiber such as pulp fiber to be formed into an approximately rectangular form seen in a planar view, a top sheet member 12 that covers the absorbent body 11 from the wearer's skin side, and a back side sheet member 13 that covers the absorbent body 11 from the wearer's non-skin side and also serving as the outer covering of the diaper 1. The absorbent body 11 may include superabsorbent polymer. The top sheet member 12 is, for example, liquid permeable non-woven fabric whose planar size is larger than the absorbent body 11. Further the back side sheet member 13 is a liquid impermeable sheet whose planar size is larger than the absorbent body 11, and as an example, sheet 13 of a two-layer structure with a liquid impermeable leakproof sheet 14 such as polyethylene, and an outer covering sheet 15 such as non-woven fabric bonded together can be given. The backsheet member 13 and the top sheet member 12 are bonded in a frame-like form sandwiching the absorbent body 11 therebetween, at a part sticking out to the outside from the four sides of the absorbent body 11 thereby forming the absorbent body 10.

Note that, as shown in FIG. 1B, liquid permeable sheet 16 such as tissue paper can be interposed between the top sheet member 12 and the absorbent body 11 or between the backsheet member 13 and the absorbent body 11. Further, elastic members 17 such as elastic strings can be interposed and fixed in an extended state along the longitudinal direction between the leakproof sheet 14 and the cover sheet 15 at both end portions in the width direction of the backsheet member 13. In this way, elasticity is imparted to the parts around the leg encircling openings 5, 5 of the diaper 1 to form a gather portion around the legs with these elastic members 17.

The abdominal-side band 20 and the back-side band 24 are both made with, for example, elements of soft sheets such as nonwoven fabric. As shown in FIG. 1B, the band members 20 and 24 are configured with two overlapping sheets of nonwoven fabric 21, 21 and the band members 20 and 24 are respectively bonded to be fixed to the corresponding end portions 10e, 10e along the longitudinal direction of the main absorbent body 10. Further, an elastic member such as a rubber string can be fixed in a extended state to each of the band members 20 and 24 to impart elasticity to these band members 20 and 24.

Such a diaper 1 is completed by using any of the aforementioned component as base material that continuously moves along the manufacturing line, and attaching and the like various components to this base material. The manufacturing device 31 according to the first embodiment performs one process among these.

Figure 2:
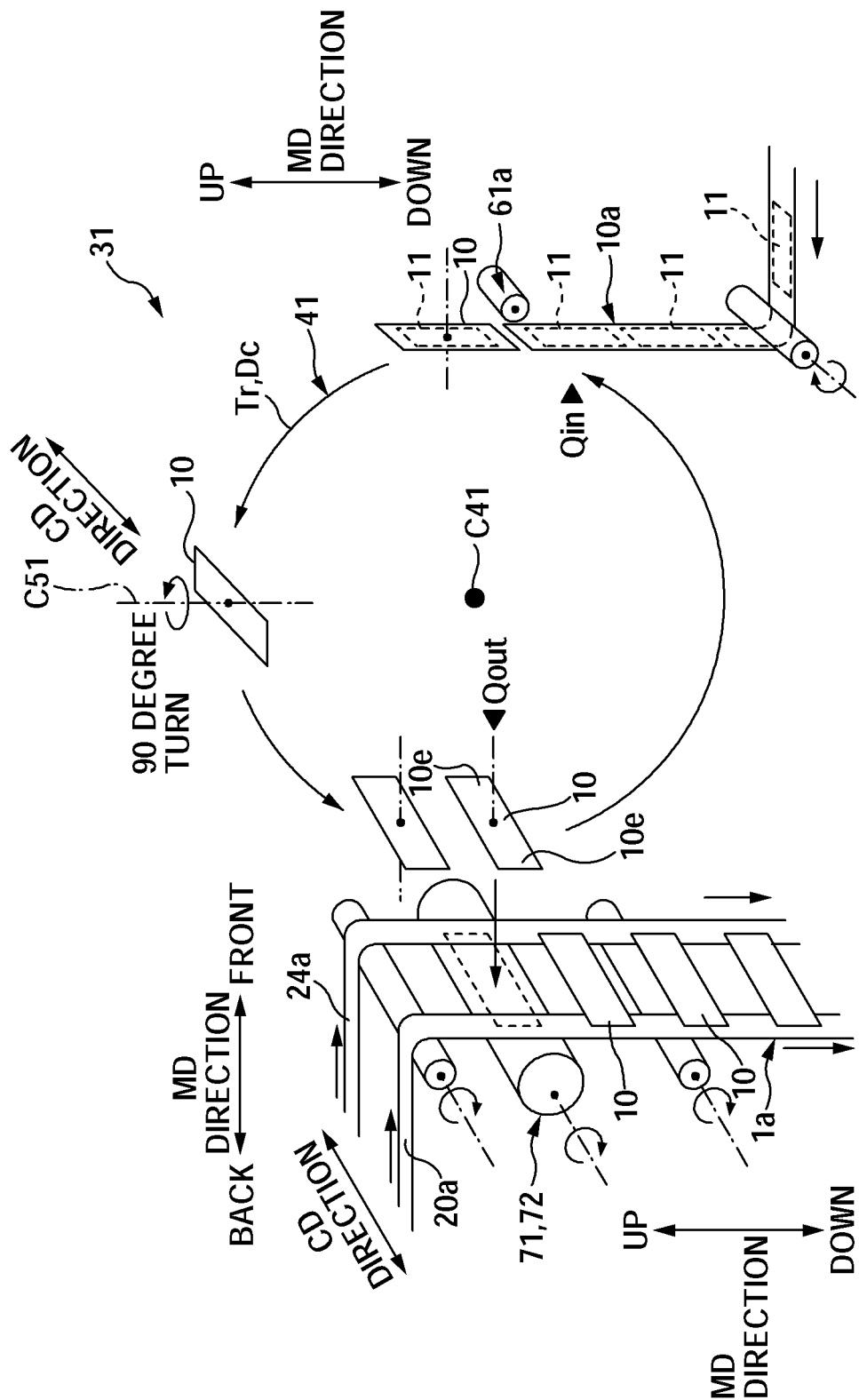
FIG. 2 is a schematic perspective diagram of a process performed by the manufacturing device 31 according to the first embodiment.
Figure 3:
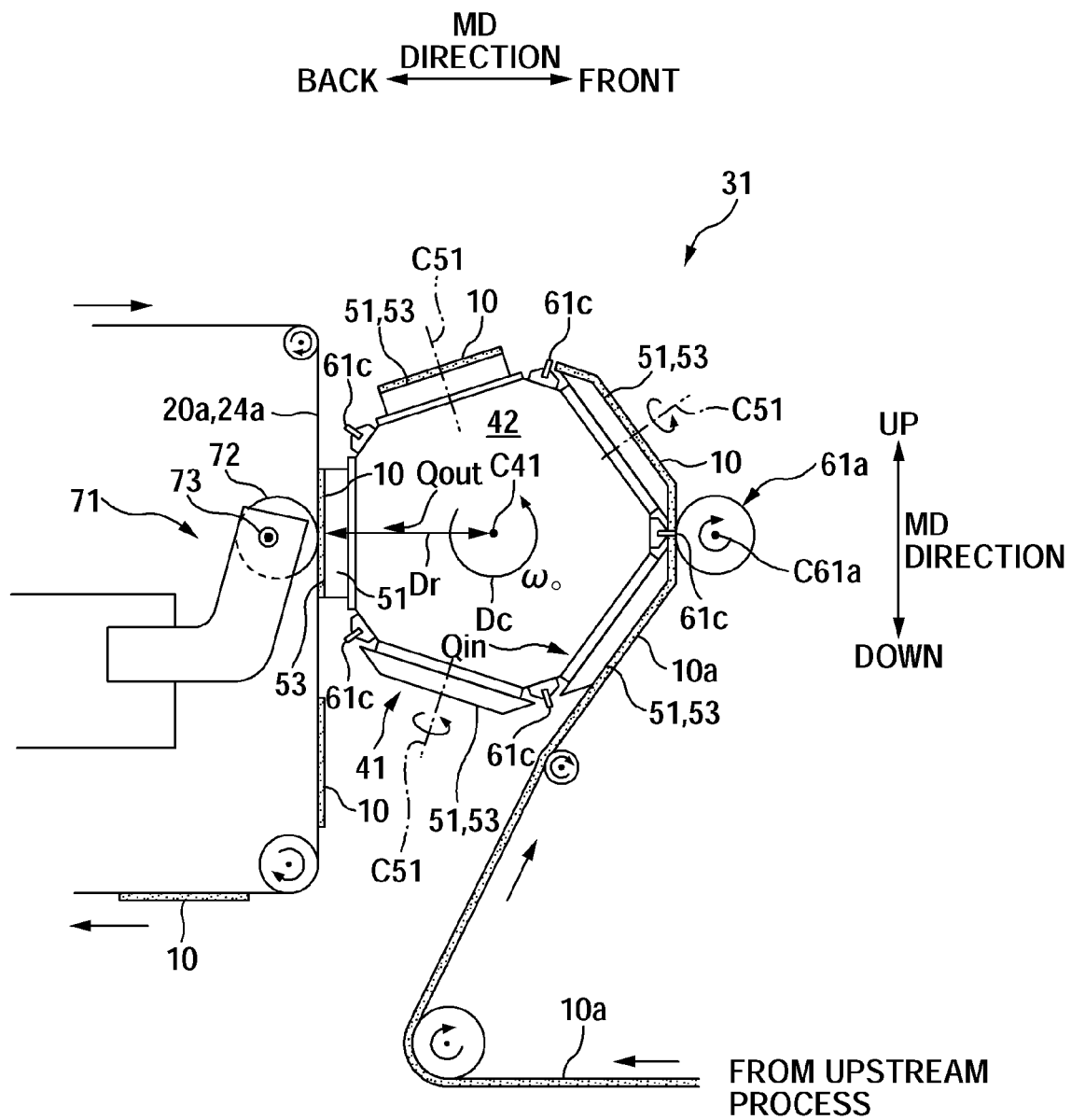
FIG. 3 is a schematic side view of the manufacturing device 31.

FIG. 2 is a schematic perspective diagram of a process performed by this manufacturing device 31. Additionally, FIG. 3 is a schematic side view of the manufacturing device 31.

Note that in the following description, the width direction of the manufacturing device 31 is referred to as also the "CD direction" and the direction orthogonal to this CD direction is referred to as also the "MD direction". In other words, the MD direction refers to any direction within a plane orthogonal to the CD direction. And in some cases, two directions orthogonal to each other within the MD direction may be respectively referred to as the "up-down direction" and the "front-back direction".

In this process, an operation of spanning the main absorbent body 10 between the pair of band members 20 and 24 to bond thereto is performed and thereby the semi-processed product 1a of the diaper 1 is made to an approximately H shape as shown in FIG. 1A.

Specifically, as shown in FIG. 2, the pair of band members 20 and 24 at the point of being supplied to the manufacturing device 31 is in a form of continuous bodies 20a, 24a in the MD direction and at the same time, continuously transported side by side in the CD direction with space therebetween. The main absorbent body 10 is also continuously transported in a form of a continuous body 10a continuous in the MD direction. In other words, the top sheet member 12 and the back side sheet member 13 that compose the main absorbent body 10 are in continuous sheet forms continuing in the longitudinal direction of the main absorbent body 10. And the top sheet member 12 and the back side sheet member 13 have interposed therebetween the absorbent body 11 while the absorbent bodies 11, 11 . . . are in a state disposed intermittently in the aforementioned longitudinal direction.

Meanwhile, the manufacturing device 31 has a rotating drum 41 that is driven to rotate about the rotation axis C41 in the CD direction. Firstly, at a receiving position Qin set at a predetermined location in its rotation direction Dc, the continuous body of the main absorbent body 10a is received by the outer circumferential face of the rotating drum 41 and adsorbed to this outer circumferential face to be retained.

Here, a cutter roller 61a is positioned at a predetermined location in the rotation direction Dc of the rotating drum 41. Additionally, receivers 61c, 61c . . . are set at predetermined intervals to the outer circumference of the rotating drum 41 (see FIG. 3) for receiving the cutter blades (not shown) of the cutter roller 61a. And the locations where the receivers 61c are set, are locations of the parts between the absorbent bodies 11, 11 associated with the continuous body of the main absorbent body 10a retained by the rotating drum 41.

Therefore, when the receivers 61c on the rotating drum 41 passes the location where the cutter roller 61a is placed, the continuous body of the main absorbent body 10a is divided along the CD direction at parts between the absorbent bodies 11, 11 thereby creating the main absorbent body 10 whose longitudinal direction is in the MD direction. And as shown in FIG. 2, the rotating drum 41 while its outer circumferential face retains the aforementioned main absorbent body 10, moves the main absorbent body 10 to the predetermined hand over position Qout by driving the rotating drum 41 to rotate.

Note that this process of moving the main absorbent body 10 to the hand over position Qout (corresponding to the workpiece hand over position) includes an operation of rotating the main absorbent body 10 by 90 degrees about the center of its surface thereby changing the longitudinal direction of the main absorbent body 10 from the MD direction to the CD direction.

Meanwhile, a hand over mechanism 71 is positioned at this hand over position Qout. The hand over mechanism 71 has a transport roller 72. And the pair of continuous bodies of band members 20a and 24a side by side in the CD direction are made to come into contact with this transport roller 72 and these continuous bodies 20a and 24a are continuously transported in the MD direction. Therefore, when the main absorbent body 10 passes the aforementioned hand over position Qout by driving the rotating drum 41 to rotate, the pair of continuous bodies of band members 20a and 24a are bonded to the two end portions 10e, 10e in the longitudinal direction of the main absorbent body 10 thereby creating the semi-processed product la in an approximately ladder form shown in FIG. 2 being the step prior to the approximately H shape shown in the aforementioned FIG. 1A.

The processes so far are those that this manufacturing device 31 is in charge of. By the way, in this example, the main absorbent body 10 corresponds to the "workpiece", and the pair of continuous bodies of band members 20a and 24a correspond to the "continuous sheet like member", and the approximately ladder form semi-processed product la corresponds to the "composite body of continuous sheet-like member". Hereinafter, description on the components 61a, 41, 71 of this manufacturing device 31 will be given.

<<<Cutter Roller 61a>>>

As shown in FIG. 3, the cutter roller 61a is driven to rotate about the shaft center C61a in the direction along the CD direction (the direction orthogonal to the plane of the paper). And planar cutter blades (not shown) are provided in the CD direction on the outer circumferential face of the cutter roller 61a. Additionally, as mentioned above, the receivers 61c that receive these cutter blades are provided between two of the later described retaining pads 51, 51 on the outer circumferential face of the rotating drum 41.

In this way, when the receivers 61c on the rotating drum 41 passes the location where the cutter roller 61a is positioned, the cutter roller 61a driven to rotate makes the cutter blades sandwich the continuous body of the main absorbent body 10a while opposing the receivers 61c thereby dividing the continuous body of the main absorbent body 10a at the location of the border between the retaining pads 51, 51 to create the main absorbent bodies 10.

<<<Rotating Drum 41>>>

The rotating drum 41 includes a main body of the rotating drum 42 (corresponding to the rotating body) that is driven to rotate about the rotation axis C41 in the CD direction and a plurality (five in the example shown in the drawing) of retaining pads 51, 51 . . . (corresponding to the workpiece retaining portion), for retaining the main absorbent body 10, supported side by side along the rotation direction Dc at intervals of a predetermined angle on the outer circumferential face of the main body of the rotating drum 42.

The main body of the rotating drum 42 is, for example, a cylindrical member whose sectional shape in the longitudinal direction is approximately a regular pentagon. And an appropriate driving source such as a motor and the like is used to drive the main body of the rotating drum 42 to rotate at, for example, a predetermined angular velocity of ω0 with the anti-clockwise direction as the direction of rotation Dc. Thereby, the retaining pads 51, 51 . . . move at a traveling speed based on the aforementioned angular velocity of ω0 along the orbit Tr (see FIG. 2) of a perfect circle with the aforementioned rotation axis C41 as the center.

The aforementioned receiving position Qin and the hand over position Qout are set along this orbit Tr as shown in FIG. 3. Therefore, the retaining pad 51 receives the continuous body of the main absorbent body 10a transported from the upper process at the receiving position Qin and bonds the main absorbent body 10 on the retaining pad 51 to the pair of continuous bodies of band members 20a and 24a to be handed over to the hand over mechanism 71 cooperating with the transport roller 72 at the hand over position Qout. By the way, it is a matter of course that the portion subject to this bonding has adhesive provided in advance.

Figure 4A:
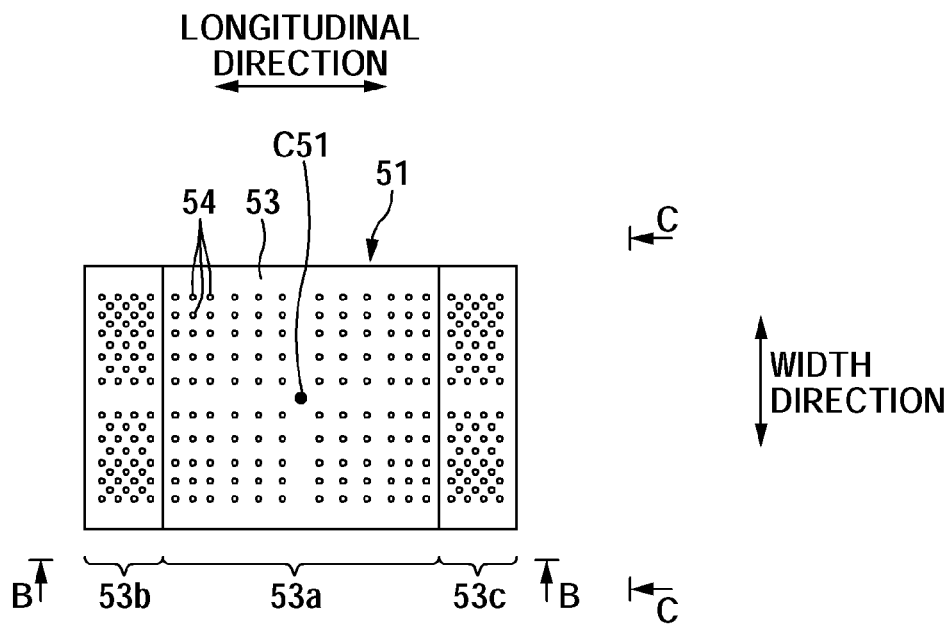
FIG. 4A is a front view (view seen from the outer side along the direction of the radius of gyration Dr) of the retaining pad 51.
Figure 4B:
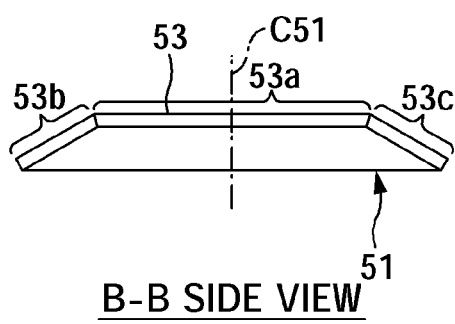
FIG. 4B is a sectional view seen from line B-B of FIG. 4A.
Figure 4C:
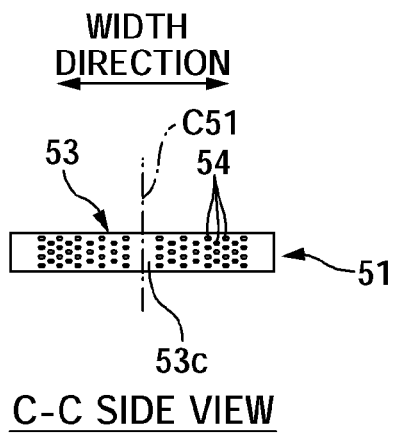
FIG. 4C is a sectional view seen from line C-C of FIG. 4A.

FIG. 4A is a front view (view seen from the outer side along the direction of the radius of gyration Dr) of the retaining pad 51 and FIGS. 4B and 4C are sectional views seen from line B-B and line C-C of FIG. 4A respectively.

The retaining pad 51 is in an approximately rectangular plate like form having the retaining face 53 that retains the main absorbent body 10 in a state where the surfaces come into contact. And the retaining surface 53 faces the outer side in the direction of the radius of gyration Dr of the main body of the rotating body 42 as shown in FIG. 3.

As shown in FIG. 4A, the retaining surface 53 has a plurality of air intake holes 54, 54 . . . formed along the entire face thereof and theses air intake holes 54, 54 . . . are connected to a negative pressure source, not shown, through an air intake chamber or an appropriate duct and the like, not shown, inside the retaining pad 51. Therefore, a suction force for retaining the main absorbent body 10 is generated on this retaining surface 53 based on air intake through the air intake holes 54, 54 . . . This air intake operation is performed along the area between the receiving position Qin and the hand over position Qout shown in FIG. 3 and is generally not performed at areas besides this (that is, the returning area between the hand over position Qout and the receiving position Qin).

As shown in FIGS. 4A through 4C, an axis of rotation C51 is set for revolving the retaining pads 51 and this axis of rotation C51 runs through the plane center of the retaining surface 53 in a direction along the direction of the radius of gyration Dr of the rotating body 42. And the retaining pads 51 are allowed to rotate around the axis of rotation C51 by an appropriate driving source (not shown) such as a motor.

Therefore, as shown in FIG. 3, the retaining pads 51 rotate 90 degrees about the axis of rotation C51 after passing the location where the cutter roller 61a is positioned thereby sequentially having the longitudinal direction of the main absorbent bodies 10 changed from the MD direction to the CD direction. And after handing over the main absorbent body 10 at the hand over position Qout, the retaining pads 51 are rotated 90 degrees to receive the continuous body of the main absorbent body 10a at the receiving position Qin. And in this way, the longitudinal direction of the retaining pad 51 returns from the CD direction to the MD direction.

Note that, as shown in FIG. 4A, the retaining surface 53 also has a longitudinal direction and a width direction among which the longitudinal direction is in line with the longitudinal direction of the retaining pad 51. Additionally, as shown in FIG. 4B, the retaining surface 53 is formed to have the central part 53a in the longitudinal direction to protrude outward in a direction parallel with the axis of rotation C51 compared with the two end parts 53b, 53c. Thereby, when this longitudinal direction is in a state facing the MD direction, as the retaining pad 51 shown on the right side in FIG. 3, the contour shape of the retaining surface 53 is in a form that is approximately along the orbit Tr of the retaining surface 53. Therefore, the speed at which each of the portions of the retaining surface 53 passes the receiving position Qin can be kept at approximately constant thereby allowing the continuous body of the main absorbent body 10a sent from the upper process to the receiving position Qin can be received in a extended state with approximately no wrinkles along the entire length in the longitudinal direction (oriented in the MD direction at the receiving position Qin) of the retaining surface 53.

Meanwhile, as shown in FIG. 4C, the retaining surface 53 is formed planar in its width direction. Therefore, the continuous body of the main absorbent body 10a can be received in an extended state with approximately no wrinkles along the entire length (entire width) in the width direction (oriented in the CD direction at the receiving position Qin) when receiving the continuous body of the main absorbent body 10a at the receiving position Qin shown in FIG. 3.

By the way, as an example of this form of the retaining surface 53 in the first embodiment, the retaining surface 53 is shown with a planar central part 53a in the longitudinal direction with the aforementioned direction of the radius of gyration Dr as the normal line and the two end parts 53b, 53c thereof with a planar inclined surface (tapered surface), however, the retaining surface 53 is not limited to such.

<<<Hand Over Mechanism 71>>>

FIGS. 5A through 5C are explanatory diagrams of the hand over mechanism 71 positioned at the hand over position Qout. FIG. 5A shows a schematic side view, FIG. 5B shows a sectional view taken along line B-B of FIG. 5A, and FIG. 5C shows a sectional view taken along line C-C of FIG. 5A.

The hand over mechanism 71 has the pair of continuous bodies of band members 20a and 24a come into contact thereto and includes the transport roller 72 (corresponding to the roller) that transports these continuous bodies 20a and 24a and a pushing mechanism 78 that pushes the outer circumferential face of the transport roller 72 toward the main body of the rotating drum 42 to press these continuous bodies 20a, 24a against then main absorbent body 10 on the retaining surface 53.

The transport roller 72 is a roller with its section in a shape of a perfect circle and is rotatably supported with the rotational shaft 73 oriented in the CD direction as the center of rotation.

The pushing mechanism 78 includes an eccentric shaft 73 provided as the aforementioned rotational shaft 73 of the transport roller 72, a servo motor 79 (corresponds to driving source) that drives the transport roller 72 to rotate with the eccentric shaft 73 as the center of rotation and a servo controller 180 (corresponds to controller) that controls the drive of the servomotor 79. Note that the rotational force by driving the servo motor 79 is transferred through the power transmission mechanism 80 to the eccentric shaft 73 and thereby eccentrically rotating the transport roller 72 with the eccentric shaft 73 as the center of rotation.

The eccentric shaft 73, 73, is integrally provided to the transport roller 72 and protrudes out from both ends thereof in the CD direction at a location decentered from the axis center C72 of the transport roller 72 by a predetermined amount 5 and supported via appropriate bearing members 74, 74 at a given location at the pedestal side portions 31a, 31a of the manufacturing device 31.

Specifically, as shown in FIG. 5A, the eccentric shaft 73 is provided at a location decentered from the axis center C72 with regard to the direction of the radius of gyration Dr of the main rotating drum body 42 that connects the rotation axis C41 of the main body of the rotating drum 42 and the aforementioned axis center C72 of the transport roller 72. In this way the transport roller 72 rotates in an eccentric manner. In other words, the transport roller 72 during its single rotation pushes out its outer circumferential face inward the aforementioned direction of the radius of gyration Dr and draws back its outer circumferential face outward the aforementioned direction of the radius of gyration Dr. Further to put it in other words, the transport roller 72 cyclically changes the amount by which the outer circumferential face thereof is pushed out along the aforementioned direction of the radius of gyration Dr with a single rotation of the transport roller 72 as one cycle.

Figure 6A:
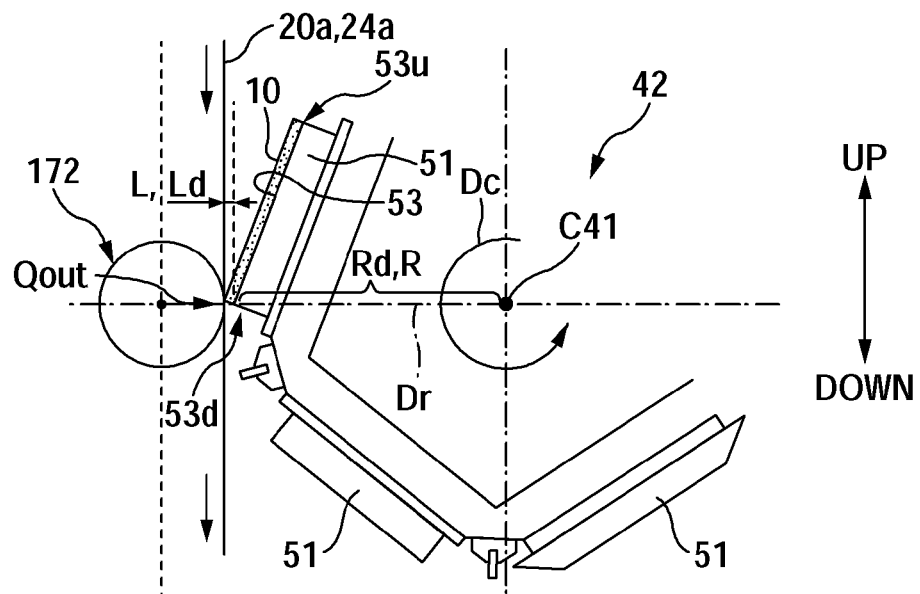
FIG. 6A is an explanatory diagram showing the reason why the transport roller 72 is eccentrically-rotated.
Figure 6B:
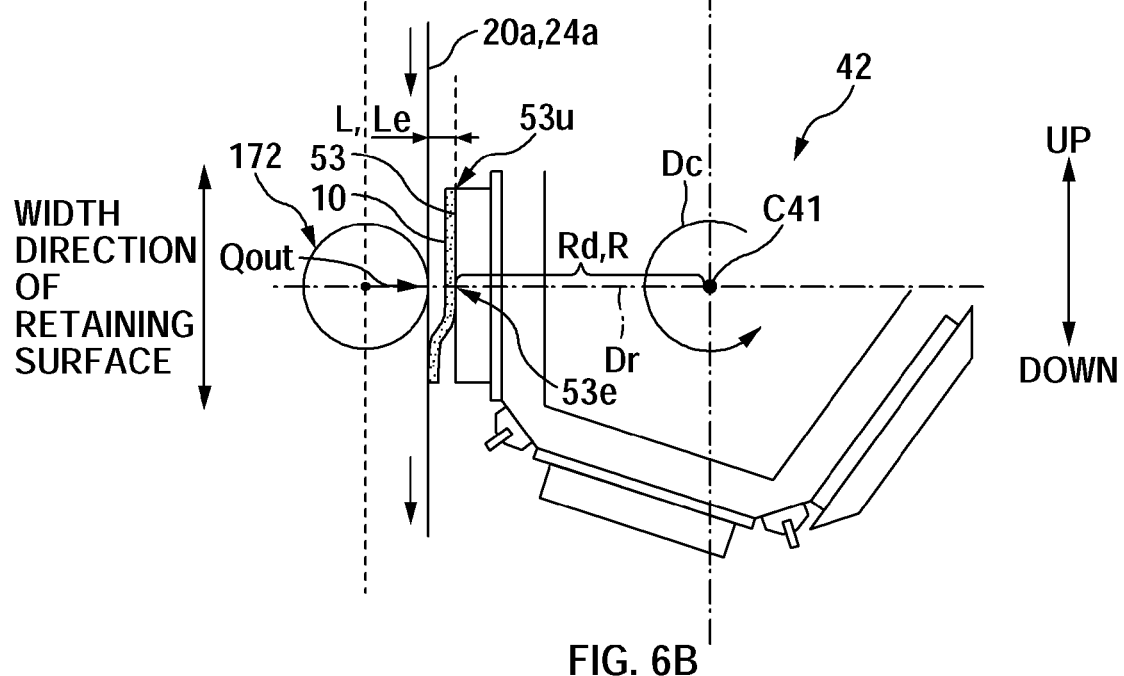
FIG. 6B is an explanatory diagram showing the reason why the transport roller 72 is eccentrically rotated.

Note that, the reason for this eccentricity is as follows. FIGS. 6A and 6B are explanatory diagrams thereof.

As described above, the retaining surface 53 is in a planar form in the width direction (see FIG. 4C). And as shown in FIG. 6B, the width of the retaining surface 53 faces the rotational direction Dc of the main body of the rotating drum 42 at the hand over position Qout. And when the retaining surface 53 hands over the main absorbent body 10, firstly as shown in FIG. 6A, the bottom stream end portion 53d in the rotational direction Dc of the retaining surface 53 passes the hand over position Qout and thereafter, the central portion 53e and the upstream end portion 53u sequentially passes the hand over position Qout as shown in FIG. 6B. However, at this time, the locations of the aforementioned direction of the radius of gyration Dr at each portions of the retaining surface 53 would differ from each other when passing the hand over position Qout due to the retaining surface 53 having a planar form in the width direction.

For example as shown in FIG. 6A, the downstream end portion 53d (or the upstream end portion 53u) of the retaining surface 53, having a large radius of gyration Rd about the rotation axis C41 of the main rotating drum body 42 would pass an outward location the radius of gyration Dr, however, the same radius of gyration Re being small at the central portion 53e shown in FIG. 6B would pass a location inward along the radius of gyration Dr.

Being the case, when the location at which the transport roller 172 is positioned does not move from a given location, distance Ld (FIG. 6A) between the downstream end portion 53d when this downstream end portion 53d passes the hand over position Qout and the outer circumferential face of the transport roller 172, and distance Le (FIG. 6B) between the central portion 53e when this central portion 53e passes the hand over position Qout and the outer circumferential face of the transport roller 172, would greatly differ. As a result, the pushing force caused from the continuous bodies of band members 20a and 24a toward the main absorbent body 10 would greatly differ at the downstream end portion 53d and the central portion 53e. Thus there is fear for poor bonding caused at one of the downstream end portion 53d and the central portion 53d.

And the same is true for each of the portions among the entire surface of the retaining surface 53, that is, the aforementioned pushing force differs at each portions of the retaining surface 53 resulting with the states of bonding differing at each of the portions of the retaining surface 53 so that poor bonding may take place at any portion as the case may be.

Hence, in this first embodiment, the transport roller 72 is eccentrically rotated to restrain the variance of this distance L. FIGS. 7A through 7F shows explanatory diagrams showing the movement of the eccentric rotation. Note that all of the drawings are seen from the side.

As the basic movement of this eccentric rotation, firstly, while a single retaining pad 51 passes the hand over position Qout, the transport roller 72 makes a single rotation in conjunction with the movement of this retaining pad 51. And during this single rotation, the amount by which the outer circumferential face of the transport roller 72 is pushed out toward the main body of the rotating drum 42 is increased (for example, FIG. 7F) when the location of the retaining surface 53 at the aforementioned direction of the radius of gyration Dr moves inward, and the amount by which the outer circumferential face of the transport roller 72 is pushed out toward the main body of the rotating drum 42 is lessened (for example, FIG. 7B or 7C) when the location of the retaining surface 53 at the direction of the radius of gyration Dr moves outward. In this way, the distance L between the retaining surface 53 and the outer circumferential face of the transport roller 72 can be maintained approximately constant.

More specifically, as shown in FIG. 7A, when the central portion 53e of the aforementioned rotational direction Dc at the retaining surface 53 passes the hand over position Qout, the amount by which the transport roller 72 is pushed out is at maximum. And as shown in FIG. 7B, the amount pushed out gradually decreases as the retaining surface 53 moves, and after the upstream end 53u of the retaining surface 53 passes, as shown in FIG. 7C, the amount pushed out is at minimum when boundary portion between the retaining pad 51 and the neighboring retaining pad 51 passes the hand over position Qout, as shown in FIG. 7D.

And further from this condition as shown in FIG. 7E, after the downstream portion 53d of the retaining surface 53 of the aforementioned neighboring retaining pad 51 passes, and the neighboring retaining pad 51 starts to pass the hand over position Qout, the amount pushed out gradually increases along with the movement and the amount pushed out is at maximum when the central portion 53e of the above retaining surface 53 passes the hand over position Qout, as shown in FIG. 7F. And this push-out movement is repeated every time the retaining pad 51 passes with such push-out movement as one cycle.

Such push-out movement is performed by controlling the drive of the servomotor 79 (corresponding to the motor) of the transport roller 72 with the servo controller 180 controls the drive. Here, the servo controller 180 is configured to be capable of performing so-called position control.

In other words, the servo controller 180 has input thereto a signal indicating a rotation angle φ from an encoder, not shown, that detects the rotation angle φ of the main body of the rotating drum 42. Similarly, a signal indicating a rotation angle θr of the transport roller 72 is also input from the encoder 174 (FIG. 8) that detects the rotation angle θr of the transport roller 72. And the servo controller 180 controls the rotation driven by the servomotor 79 so that the transport roller 72 makes a single rotation while the main body of the rotating drum 42 rotates by a rotation angle (a fifth of a single rotation, i.e., 72 degrees in the example shown) corresponding to an amount of movement of a piece of the retaining pad 51 based on these signals. That is, the transport roller 72 is controlled to be driven to rotate by a rotation angle θr being an amount equal to the number (five times in the example shown) of times of the rotation angle φ of the main body of the rotating drum 42, the number being the number of pieces of the retaining pads 51. In this way the transport roller 72 is rotated eccentrically in conjunction with the movement of the retaining pad 51.

Figure 8:
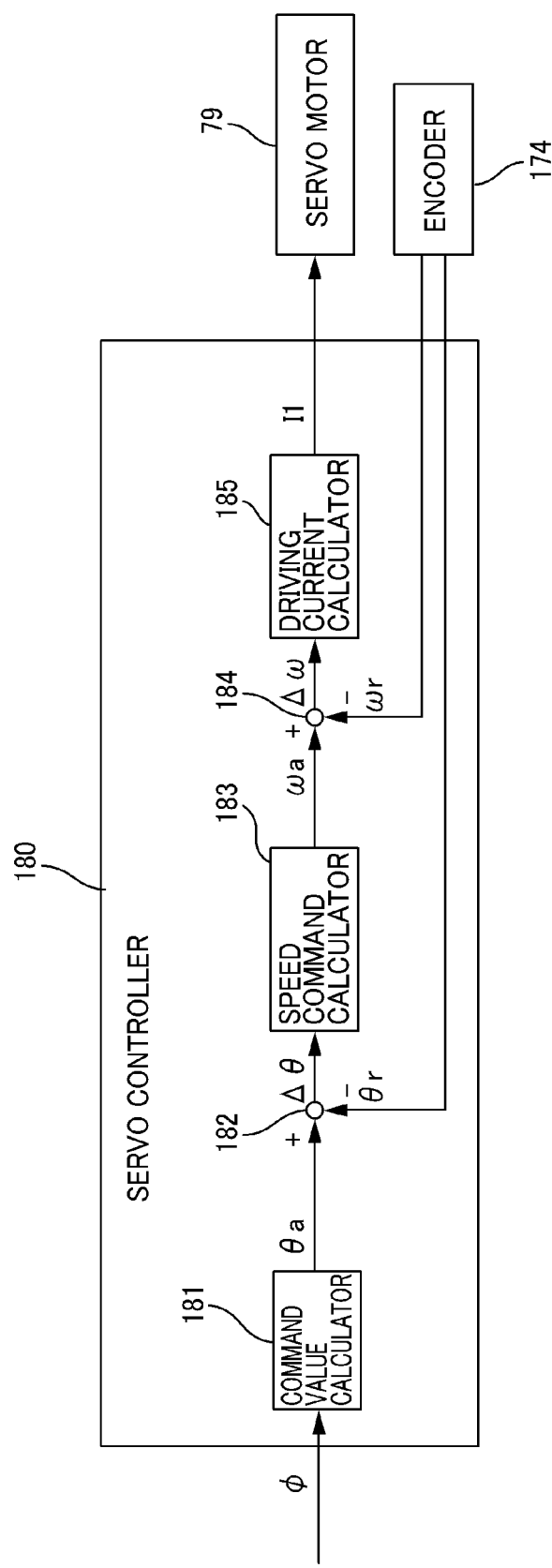
FIG. 8 is a configuration diagram of the servo controller 180.

FIG. 8 is a configuration diagram of the servo controller 180. The servo controller 180 includes a command value calculator 181, a position comparator 182, a speed command calculator 183, a speed comparator 184, and a driving current calculator 185.

The command value calculator 181 calculates the command value θa of the rotation angle of the transport roller 72 based on the actual value φ of the aforementioned rotation angle input from the encoder of the main body of the rotating drum 42. This calculation is performed by, for example, multiplying the actual value φ of the rotation angle of the main body of the rotating drum 42 by the numbers of times (five times in the example shown) the number of retaining pads equipped to the main body of the rotating drum 42, and the calculated value (=5×φ) resulting from this calculation is set as the command value θa of the rotation angle of the transport roller 72. Next, the position comparator 182 compares the command value θa of this rotation angle with the actual value θr of the rotation angle and calculates the deviation Δθ (angle deviation Δθ) between the two. Note that, the actual value θr is input from the encoder 174 of the transport roller 72 as mentioned above.

And this angle deviation Δθ is input to the speed command calculator 183. The speed command calculator 183 performs a predetermined calculation based on the aforementioned angle deviation Δθ and obtains the angular velocity (rotational speed) command value ωa to send this command value ωa to the speed comparator 184. Then the speed comparator 184 compares this angular velocity command value ωa with the angular velocity actual value ωr sent from the encoder 174 of the transport roller 72 to calculate the deviation Δω (angular velocity deviation Δω) between the two. Then this angular velocity deviation Δω is sent to the driving current calculator 185. The driving current calculator 185 performs a predetermined calculation based on the aforementioned angular velocity deviation Δω to obtain the value of the driving current I1 that lowers the angular velocity deviation Δω. The driving current I1 obtained, is supplied to the servomotor 79 to drive the servo motor 79.

By the way, as shown in FIG. 5B, a so-called wrapping connector driving mechanism is used in this example as the power transmitting mechanism that transmits a driving force of the servo motor 79 to rotate the transport roller 72. In other words, a pulley 79p is provided to the rotational shaft 79a driven by the servo motor 79 and a pulley 79p is also provided to one end in the CD direction of the eccentric shaft 73. Further therebetween, a relay shaft 80m is rotatably positioned in the CD direction and a first pulley 81 and a second pulley 82 are provided to one end of the relay shaft 80m. And an endless timing belt 85 is wound around both the pulley 79p of the rotational driveshaft 79a and the first pulley 81 of the relay shaft 80m, and an endless timing belt 84 is wound around both the second pulley 82 of the relay shaft 80m and the pulley 73p of the eccentric shaft 73 thereby connecting the rotational driveshaft 79a and eccentric shaft 73 via the relay shaft 80m in a manner capable of transmitting rotational force. Therefore, the rotational force of the servo motor 79 to drive the transport roller 72 is transmitted to drive the transport roller 72 to rotate.

Note that, in this example shown in FIG. 5B, a third pulley 83 is also provided to the other end of the relay shaft 80m and further, a pulley 73p is also provided to the other end in the CD direction of the eccentric shaft 73 with a timing belt 84 also wound around these pulleys 83, 73p. In this way, rotational force is input also from the other end in the CD direction of the transport roller 72 for driving via the relay shaft 80m. Thus in this case, torsion and the like of the transport roller 72 is restrained compared to the case where a rotational force for driving is input only from one end of the transport roller 72. As a result, stability of the rotational movement of the transport roller 72 can be improved.

Here as shown in FIGS. 9B and 9C, it is preferable that the transport roller 72 is a body separate from the core portion 72a to which the eccentric shaft 73 is attached with the outer portion of the core portion 72a covered with the outer circumferential portion 72b, while the outer circumferential portion 72b with bearing members 74a, 74a interposed between the core portion 72a, being rotatably provided around the axis center C72 of the core portion 72a. And further it is preferable that the sectional shape of the core portion 72a is a perfect circle with the aforementioned eccentric shaft 73, 73 provided at a location decentered by an eccentric amount 5 from its axis center C72.

And having such configuration, when the servo motor 79 drives the core portion 72a to rotate, the outer circumferential face of the outer circumferential portion 72b is pushed out and withdrawn along the direction of the radius of gyration Dr of the main rotating drum body 42 with an eccentric rotation of the core portion 72a. In this way, the distance L between the outer circumferential face of the transport roller 72 and the retaining surface 53 is kept approximately constant.

Further, with the aforementioned configuration, the outer circumferential portion 72b is relatively rotatable with regard to the core portion 72a due to the bearing materials 74a, 74a. Therefore, even when relative velocity exists between the outer circumferential face of the outer circumferential portion 72b being the outer circumferential face of the transport roller 72 and the retaining surface 53 of the retaining pad 51, this relative velocity can be quickly absorbed by the relative rotation between the outer circumferential portion 72b and the core portion 72a resulting to be capable of effectively restraining wrinkles made to the main absorbent body 10 and continuous bodies of band members 20a and 24a due to the difference in relative velocity.

Details are as follows.

Figure 10:
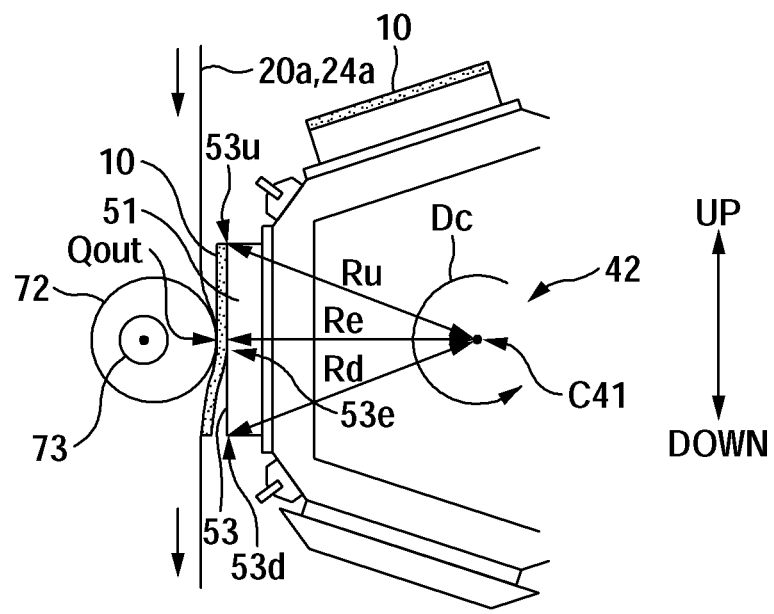
FIG. 10 is an explanatory diagram showing an operational advantage of the above preferred aspect.

For example, as shown in the side view of FIG. 10, since the radius of gyration Re is small at the central portion 53e compared with the radiuses of gyration Rd, Ru at the respective downstream end portion 53d and the upstream end portion 53u when the central portion 53e of the retaining surface 53 passes the hand over position Qout, the speed at which the central portion 53e moves in the rotational direction Dc lowers compared to these end portions 53d, 53u. However, with regard to the outer circumferential face of the transport roller 72, a portion of the outer circumferential face with a large amount of eccentricity opposes the central portion 53e of the retaining surface 53 due to the amount pushed out at this point being at maximum, makes the peripheral velocity at this portion at the outer circumferential face high. Therefore, relatively large difference in relative velocity can be generated between the central portion 53e of the retaining surface 53 and the outer circumferential face of the transport roller 72, where this difference in relative velocity creates wrinkles to the main absorbent body 10 and continuous bodies of band members 20a and 24a.

With regard to this point, when the outer circumferential portion 72b is configured to be relatively rotatable with regard to the core portion 72a as mentioned above, the outer circumferential portion 72b comes into contact with the continuous bodies of band members 20a and 24a or the main absorbent body 10 and is imparted rotational force from this contact, and are driven to rotate in accordance to the movement of the retaining surface 53. Thereby, the difference in relative velocity between the outer circumferential face of the transport roller 72 and the retaining surface 53 is effectively restrained.

Further as shown in FIG. 9C, it is preferable that the contour shape of the outer circumferential portion 72b is in a form that accords with the form of the surface of the retaining surface 53 of the retaining pad 51. For example, in this first embodiment, the form of the surface of the retaining surface 53 at the hand over position Qout is, as mentioned above, in a form where the central part 53a in the CD direction protrudes outward in the direction of the radius of gyration Dr (direction parallel to the axis of rotation C51) compared with the end parts 53b, 53c located at both sides thereof.

Therefore in this example, the contour shape of the outer circumferential portion 72b is in a drum shape where the center portion is concaved compared to the two sides in the CD direction. And with such form, the continuous bodies of band members 20a and 24a can be surely pushed against the main absorbent body 10 with the outer circumferential portion 72b and the retaining surface 53 thus improving the bonding performance.

Figure 11:
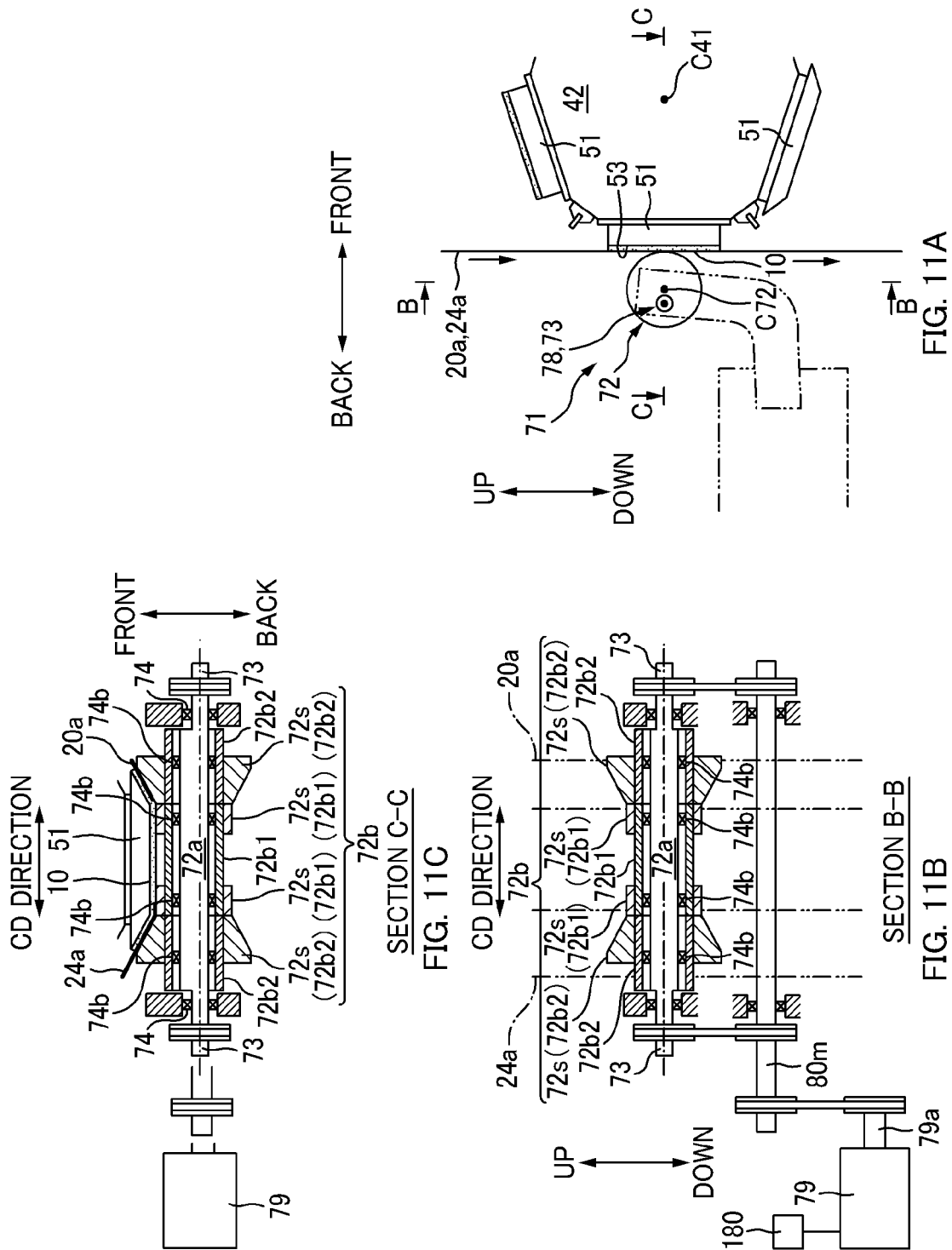
FIG. 11A is a schematic side view of a preferred aspect of the transport roller 72 associated with the hand over mechanism 71.
FIG. 11B is a sectional view taken along line B-B of FIG. 11A.
FIG. 11C is a sectional view taken along line C-C of FIG. 11A.

By the way, in this case, it is further preferable that the outer circumferential portion 72b is divided into a plurality of cylindrical members 72b2, 72b1, 72b2 along the CD direction while each of the cylindrical members 72b2, 72b1, 72b2 are rotatably supported by the core portion 72a via bearing members 74b, 74b..., as shown in FIGS. 11B and 11C. In the example shown, the outer circumferential portion 72b is composed of three cylindrical members being cylindrical member 72b1 for the center part in the CD direction and cylindrical members 72b2, 72b2 for the end parts in the CD direction.

And with this configuration, each of the cylindrical members 72b2, 72b1, 72b2 rotate independently as followers. Therefore as in the aforementioned case where the outer circumferential portion 72b is in a drum shape with the external diameters differing depending on the location along the CD direction, can relieve the problem of differences in relative velocity that may occur between the portions having different external diameters.

Further, it is preferable that the surface layer portion 72s including the outer circumferential face of the transport roller is formed with an elastic material having flexibly to be elastically deformed. In each of the examples shown in FIGS. 5A through 5C, the examples shown in FIGS. 9A through 9C, and the examples shown in FIGS. 11A through 11C, the surface layer portion 72s of the transport roller 72 is formed with elastic members. Sponge-like polyurethane rubber can be given as an example of the material used for this elastic member.

And with the above configuration, the difference in relative velocity between the transport roller 72 and the retaining surface 53 can be absorbed by also the elastic deformation of the surface layer portion 72s so that wrinkles on the main absorbent body 10 and continuous bodies of band members 20a and 24a can be further effectively restrained. Further, severe damages on the main absorbent body 10 and continuous bodies of band members 20a and 24a sandwiched between the retaining surface 53 and the outer circumferential face of the transport roller 72 at the time of hand over can be avoided.

—Second Embodiment—

Figure 12:
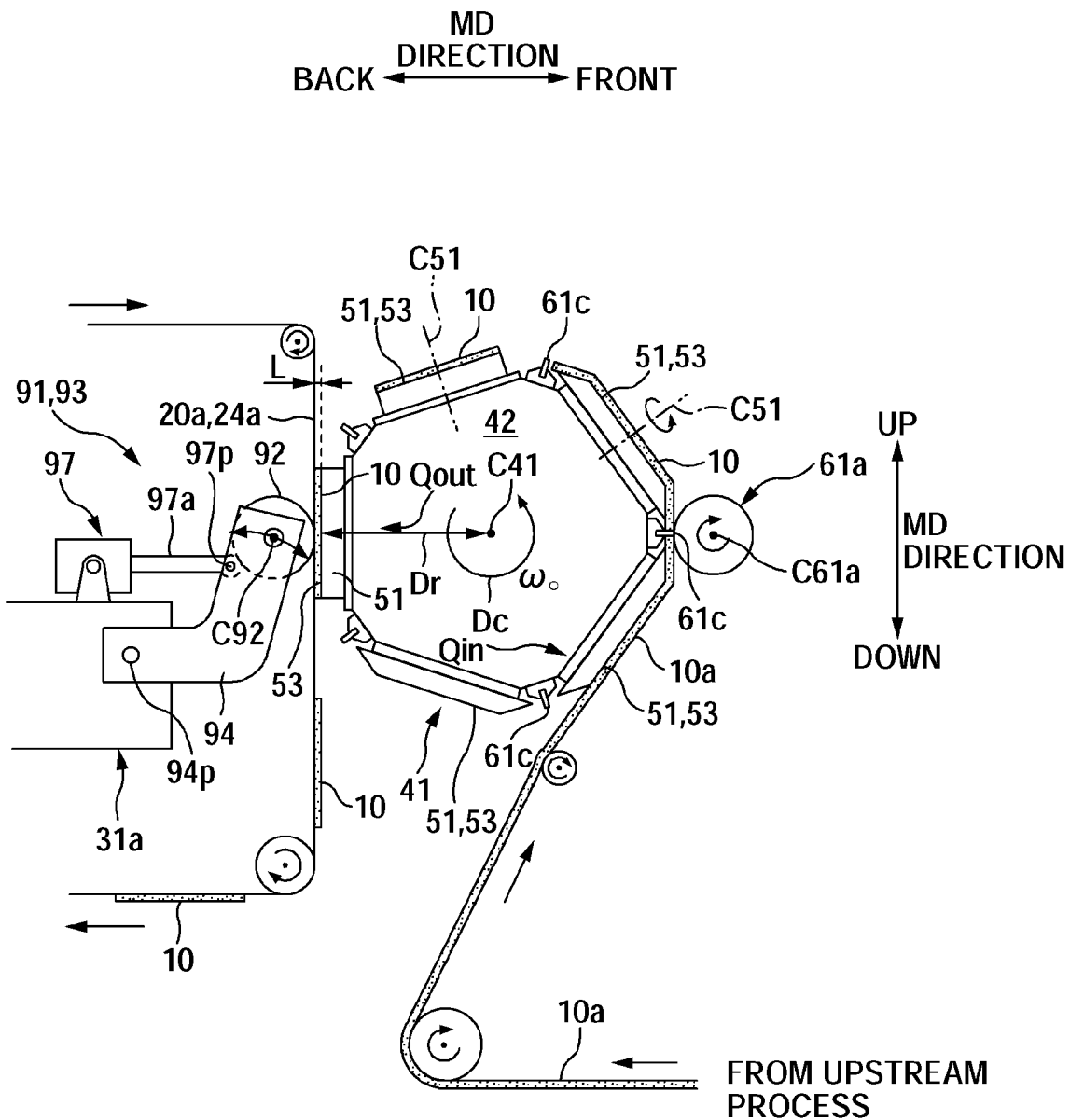
FIG. 12 is a schematic side view of the hand over mechanism 91 according to the second embodiment.

FIG. 12 is an explanatory diagram showing a side view of the hand over mechanism 91 according to the second embodiment.

In the first embodiment, the transport roller 72 was rotated eccentrically using the eccentric shaft 73 in the pushing mechanism 78 of the hand over mechanism 71, however, the second embodiment differs from the first embodiment in that a rocking arm 94 is used to perform the pushing movement of the outer circumferential face of the transport roller 92. Note that the others are approximately the same as the first embodiment thus explanation will be given hereunder only on the differences and explanation on the same configurations are omitted.

As shown in FIG. 12, the hand over mechanism 91 includes as the pushing mechanism 93, a rocking arm 94 that supports the transport roller 92, and a driving mechanism 97 that rocks the end portion of the rocking arm 94 that supports the transport roller 92 in the direction of the radius of gyration Dr of the main rotating drum body 42.

The rocking arm 94 is, for example, supported by a coupling pin 94p with one end thereof at a given location at the pedestal side portion 31a of the manufacturing device 31. And the other end portion is configured to be capable of rocking with this coupling pin 94p as the fulcrum. On the other hand, the other end portion has the transport roller 92 with a perfect circular section provided rotatable about its axis center C92 via a bearing member not shown. And the pair of rocking arms 94, 94 are provided side by side in the CD direction with which the transport roller 92 is supported at the two ends in the CD direction.

For example, a cylinder member 97 such as, for example, a hydraulic cylinder or an air cylinder is used as the driving mechanism 97. And the tip portion of the piston 97a of the cylinder member 97 is connected to the other end of portion of the rocking arm 94 via a coupling pin 97p. Therefore, the other end portion of the rocking arm is rocked by the piston 97a moving in a telescopic manner based on the control of the working fluid such as working oil and compressed air thereby advancing and withdrawing the transport roller 92 at the other end portion in the direction of the radius of gyration Dr of the main body of the rotating drum 42.

The movement of this advancing and withdrawing is basically the same as that in the case of the first embodiment. In other words, the transport roller 92 is advanced toward the main body of the rotating drum 42 when the position of the retaining surface 53 at the hand over position Qout moves inward along the direction of the radius of gyration Dr of the main body of the rotating drum 42, whereas the transport roller is withdrawn when the position of the retaining surface 53 moves outward along the direction of the radius of gyration Dr. In this way, the distance L between the retaining surface 53 and the outer circumferential face of the transport roller 92 can be maintained approximately constant.

Note that, the transport roller 92 maybe configured as a slave roller that rotates as followers, or may be configured as a driving roller that is driven to rotate by an appropriate driving source such as a motor.

By the way, an elastic member such as a spring member, not shown, may be used instead of the cylinder member 97 provided to this rocking arm 94. That is, an elastic force may be imparted by this elastic member so that the transport roller 92 is permanently pushed toward and against the main body of the rotating drum 42. In this case, the transport roller 92 would be passively moving back and forth along the direction of the radius of gyration Dr such that the transportation roller 92 is pushed from the retaining surface 53 along the aforementioned direction of the radius of gyration Dr in accordance with to the changes in the position of the retaining surface 53 along the aforementioned direction of the radius of gyration Dr.

—Other Embodiments—

Hereinabove, description was given of embodiments of the present invention, however, the present invention is not limited to such embodiments and may be modified in the following ways.

In the aforementioned embodiment, transport rollers 72, 92 having sectional shapes with perfect circles were shown as examples, however, the sectional shape of the transport rollers 72, 92 are not limited to such and may be changed appropriately according to the relation between the geometry of the retaining surface 53 of the retaining pad 51. For example, a roller with an oval sectional shape can be used depending of the geometry of the retaining surface 53.

In the aforementioned first embodiment, the servo controller was driven to rotate the transport roller 72 by increasing the speed to a rotation angle θr being an amount equal to the number (five times in the example shown) of times of the rotation angle φ of the main body of the rotating drum 42, the number being the number of pieces of the retaining pads 51. That is, the transport roller 72 was driven to rotate proportional to an angular velocity $\omega 0$ of the main body of the rotating drum 42, being five times the angular velocity thereof, however, the speed is not limited to such. For example, the speed may be cyclically varied from an angular velocity that is five times the angular velocity $\omega 0$. In other words, the angular velocity may be varied according to the position of the aforementioned direction of the radius of gyration Dr of the retaining surface 53 at the hand over position Qout.

To give an example, the angular velocity of the transport roller 72 is reduced as the amount by which the outer circumferential face of the transport roller 72 is pushed out toward the main body of the rotating drum 42 is increased when the position of the main body of the rotating drum 42 at the aforementioned direction of the radius of gyration Dr moves toward the inside. And the angular velocity of the transport roller 72 is increased as the amount by which the outer circumferential face of the transport roller 72 is pushed out is reduced when the position of the main body of the rotating drum 42 at the aforementioned direction of the radius of gyration moves toward the outside.

And being the case, the difference in relative velocity between the retaining surface 53 and the transport roller 72 described-above with reference to FIG. 10 can be reduced and as a result, wrinkles and the like made to the main absorbent body 10 and continuous bodies of band members 20a and 24a due to the difference in relative velocity can be effectively restrained.

Figure 13:
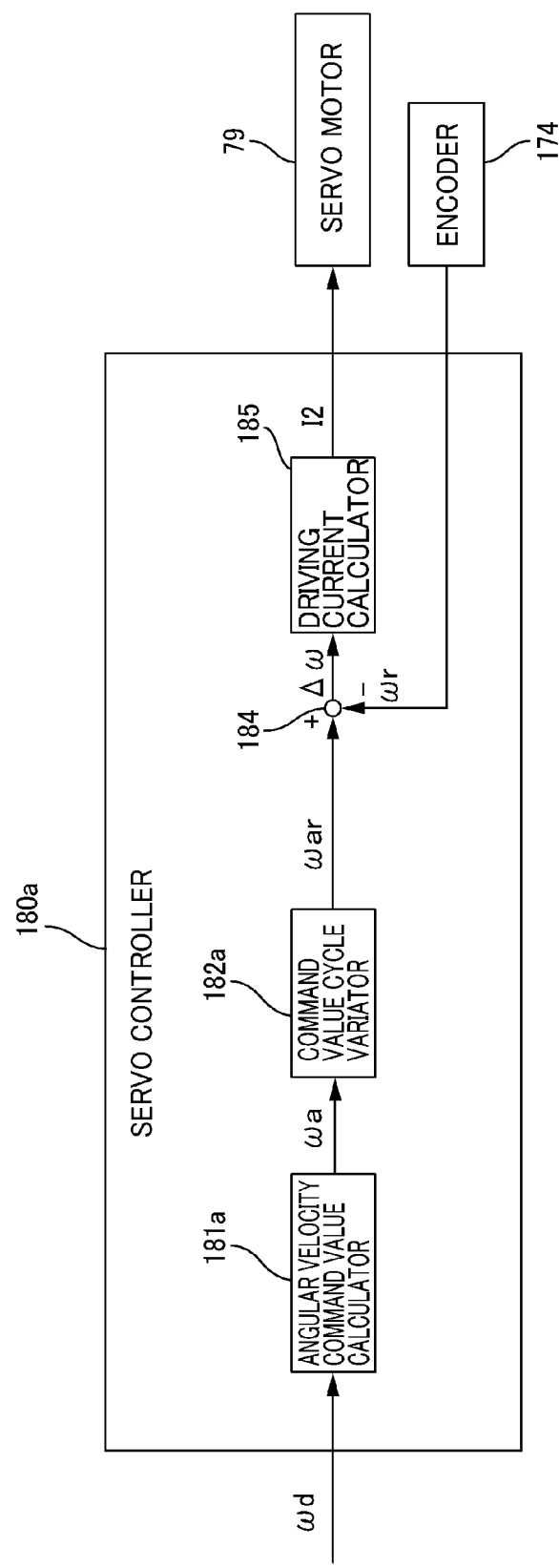
FIG. 13 is a configuration diagram of the servo controller 180a according to another embodiment.

Note that, the servo controller 180a that cyclically changes the angular velocity of the aforementioned transport roller 72 is, for example, realized by a controller that performs speed control. FIG. 13 shows a configuration thereof.

The servo controller 180a includes an angular velocity command value calculator 181a, a command value cyclic variator 182a, a speed comparator 184, and a driving current calculator 185.

The angular velocity command value calculator 181a calculates a temporary angular velocity command value $\omega a$ of the transport roller 72 based on the angular velocity actual value $\omega d$ of the main body of the rotating drum 42 input from the encoder of the main body of the rotating drum 42. This calculation is performed by multiplying the numbers (five times in the example shown) of the retaining pads 51 equipped to the main body of the rotating drum 42 by the above-described actual value $\omega d$, and the calculated value ($=5\times\omega d$) resulting from this calculation is set as the temporary angular velocity command value $\omega a$ of the transport roller 72.

Next, the command value cyclic variator 182 makes a calculation by adding a predetermined function $f(\theta r)$ to the above-described temporary angular velocity command value $\omega a$, and sends this calculated value ($=\omega a+f(\theta r)$) as the real angular velocity command value $\omega ar$ to the speed comparator 184. Here, similar to the case in the above-described first embodiment, θr is calculated by multiplying the number (five times in the example shown) of the retaining pads 51 equipped to the main body of the rotating drum 42 by the rotation angle actual value ϕ of the main body of the rotating drum 42 sent from the encoder (θr=5×ϕ). Additionally, function f (θr) is an appropriate function that varies with the angle of θr between zero degrees and 360 degrees as one cycle, and an example thereof is shown in the following equation (1).

$$f(\theta r)=A\times\sin(2\pi/360\times\theta r) \quad (1)$$

Note that, A is an appropriate constant.

Next, the speed comparator 184 compares this real command value ωar with the angular velocity actual value ωr sent from the encoder 174. Then the deviation Δω(angular velocity deviation Δω) between the two is calculated for this angular velocity deviation Δω to be sent to the driving current calculator 185. Then the driving current calculator 185 performs a given calculation based on this angular velocity deviation Δω to obtain the value of the driving current I2 that makes this angular velocity deviation Δω small. And the driving current I2 obtained is supplied to the servo motor 79 to drive the servo motor 79.

In the aforementioned first embodiment, the transport roller 72 associated with the hand over mechanism 71 was driven to rotate by an exclusive servomotor 79, however, it is not limited to such. For example, the transport roller 72 may be rotated by transmitting the rotational movement of the motor that drives the main body of the rotating drum 42 about the rotation axis C41, through an appropriate rotational movement transmitting mechanism to the transport roller 72. Note that an appropriate train of gears, a cam mechanism and the like can be given as an example of the rotational movement transmitting mechanism, however, it is not limited to such as long it is a mechanism capable of increasing the velocity of the rotational movement of the main body of the rotating drum 42 by an acceleration ratio of the number of the retaining pads 51 (five times in the example shown since the number of retaining pads 51 are five) to be transmitted to the transport roller 72.

REFERENCE SIGNS LIST

1 disposable diaper, 1*a* semi-processed product (composite body of continuous sheet-like member), 3 body encircling opening, 5 leg encircling opening, 10 main absorbent body (workpiece), 10*a* continuous body of main absorbent body, 10*e* end portion, 11 absorbent body, 12 top sheet member, 13 back side sheet member, 14 leakproof sheet, 15 outer covering sheet, 16 liquid permeable sheet, 17 elastic member, 20 abdominal-side band member, 20*a* continuous body of band member (continuous sheet like member), 21 nonwoven fabric, 24 back side band member, 24*a* continuous body of band member (continuous sheet like member), 31 manufacturing device, 31*a* pedestal side portion, 41 rotating drum, 42 main body of the rotating drum (rotating body), 51 retaining pad (workpiece retaining portion), 53 retaining surface, 53*a* central part, 53*b* end part, 53*c* end part, 53*d* downstream end portion, 53*e* center portion, 53*u* upstream end portion, 54 air intake hole, 61*a* cutter roller, 61*c* receiver, 71 hand over mechanism, 72 transport roller (roller), 72*a* core portion, 72*b* outer circumferential portion, 72*b*1 cylindrical member, 72*b*2 cylindrical member, 72*s* surface layer portion, 73 rotational shaft (eccentric shaft), 73*p* pulley, 74 bearing member, 74*a* bearing member, 74*b* bearing member, 78 pushing mechanism, 79 servomotor (motor), 79*a* driven rotational shaft, 79*p* pulley, 80 power transmission mechanism, 80*m* relay shaft, 81 first pulley, 82 second pulley, 83 third pulley, 84 timing belt, 85 timing belt, 91 hand over mechanism, transport roller, 93 pushing mechanism, 94 rocking arm, 94*p* coupling pin, 97 cylindrical member (driving mechanism), 97*a* piston, 97*p* coupling pin, 172 transport roller, 174 encoder, 180 servo controller, 180*a* servo controller, 181 command value calculator, 181*a* angular velocity command value calculator, 182 position comparator, 182*a* command value cyclic variator, 183 speed command calculator, 184 speed comparator, 185 driving current calculator, C1 center, C41 rotation axis, C51 axis of revolution, C61*a* shaft center, C72 axis center, C92 axis center, Qin receiving position, Qout hand over position (workpiece hand over position), Dc rotation direction, Dr direction of radius of gyration, Tr orbit

The invention claimed is:

1. A device for manufacturing a composite body of a continuous sheet member by attaching and handing over a retained workpiece to a continuous sheet member, at a workpiece hand over position, comprising:
   a rotating body that rotates about a rotating shaft;
   a workpiece retaining portion supported by the rotating body in a state where a retaining surface that retains the workpiece faces outward from a center of the rotating body in a direction of radius of gyration of the rotating body;
   a workpiece hand over mechanism that is positioned to accord with the workpiece hand over position along a direction of rotation of the rotating body, and that hands over the workpiece from the retaining surface to the continuous sheet-like member when the retaining surface passes the workpiece hand over position, wherein
   the workpiece hand over mechanism has a roller that comes into contact with the continuous sheet-like member to transport the continuous sheet member, and a pushing mechanism that is capable of pushing an outer circumferential face of the roller inward toward the center of the rotating body along the direction of radius of gyration to push the continuous sheet member against the workpiece, and
   the pushing mechanism changes an amount by which the outer circumferential face is pushed toward the center of the rotating body in conjunction with a location, of the retaining surface along the direction of radius of gyration, at the workpiece hand over position,
   wherein
   the pushing mechanism has a driving source that moves a location of the outer circumferential face of the roller inward and outward with respect to the center of the rotating body along the direction of radius of gyration and a controller that controls the driving source.

2. The device for manufacturing a composite body of a continuous sheet-like member according to claim 1, wherein
   the pushing mechanism increases an amount by which the outer circumferential face of the roller is pushed toward the center of the rotating body at the workpiece hand over position when the location of the retaining surface moves inward along the direction of radius of gyration, and
   the pushing mechanism reduces an amount by which the outer circumferential face of the roller is pushed toward the center of the rotating body when the location of the retaining surface moves outward along the direction of radius of gyration.

3. The device for manufacturing a composite body of a continuous sheet-like member according to claim 1, wherein
   a plurality of the workpiece retaining portions are provided at a predetermined angular interval along a direction of rotation of the rotating body, the roller has as a rotating shaft, an eccentric shaft decentered from an axis center of the roller, the rotating shaft of the roller is parallel to the rotating shaft of the rotating body, and the driving source of the pushing mechanism is a motor that drives the roller to rotate with the eccentric shaft as a center of rotation, and the motor allows the roller to make a single rotation for each workpiece retaining portion.

4. The device for manufacturing a composite body of a continuous sheet-like member according to claim 3, wherein the roller has a core portion and an outer circumferential portion arranged to cover an outer circumference of the core portion, the outer circumferential portion is rotatably supported by a bearing member interposed between the outer circumferential portion and the core portion with a center of the core portion as the center of rotation, and the eccentric shaft is provided at a location decentered from the center of the core portion, and the core portion is driven to rotate with the eccentric shaft as a center of rotation.

5. The device for manufacturing a composite body of a continuous sheet member according to claim 4, wherein the outer circumferential portion is configured with a plurality of cylindrical members arranged in a direction along the rotational shaft of the roller, and the cylindrical members are each rotatably supported by the core portion via bearing members each provided for respective ones of the cylindrical members.

6. The device for manufacturing a composite body of a continuous sheet-like member according to claim 4, wherein the retaining surface of the workpiece retaining portion at the workpiece hand over position has a shape where a central part in a direction along the rotating shaft than two end portions therealong protrudes outward from the center of the rotating body along the direction of radius of gyration, and a contour shape of the roller is in a drum shape, corresponding to the shape of the retaining surface, where a central part in a direction along the rotating shaft of the roller is concaved than two end portions therealong.

7. The device for manufacturing a composite body of a continuous sheet member according to claim 3, wherein an angular velocity of the roller driven to rotate is changed in conjunction with a location, of the retaining surface along the direction of radius of gyration, at the workpiece hand over position.

8. The device for manufacturing a composite body of a continuous sheet member according to claim 1, wherein a surface layer portion of the outer circumferential face of the roller is formed by an elastic member having flexibility to deform elastically.

* * * * *